United States Patent
Bailly et al.

(10) Patent No.: US 11,903,807 B2
(45) Date of Patent: Feb. 20, 2024

(54) UMBILICAL HERNIA PROSTHESIS

(71) Applicant: SOFRADIM PRODUCTION, Trevoux (FR)

(72) Inventors: Pierre Bailly, Caluire-et-Cuire (FR); Gaetan Romuald, Bron (FR)

(73) Assignee: SOFRADIM PRODUCTION, Trevoux (FR)

(*) Notice: Subject to any disclaimer, the term of this patent is extended or adjusted under 35 U.S.C. 154(b) by 422 days.

(21) Appl. No.: 17/343,671

(22) Filed: Jun. 9, 2021

(65) Prior Publication Data
US 2021/0298887 A1 Sep. 30, 2021

Related U.S. Application Data

(60) Division of application No. 16/927,735, filed on Jul. 13, 2020, now Pat. No. 11,039,912, which is a
(Continued)

(30) Foreign Application Priority Data

Jul. 13, 2011 (FR) ..................... 11/56425

(51) Int. Cl.
*A61F 2/00* (2006.01)
*A61B 17/00* (2006.01)
(Continued)

(52) U.S. Cl.
CPC ........ *A61F 2/0063* (2013.01); *A61B 17/0057* (2013.01); *A61B 17/04* (2013.01);
(Continued)

(58) Field of Classification Search
CPC ........... A61F 2/0063; A61F 2220/0008; A61B 2017/00597; A61B 2017/00623; A61B 2017/0496
See application file for complete search history.

(56) References Cited

U.S. PATENT DOCUMENTS

| | | | |
|---|---|---|---|
| 1,187,158 | A | 6/1916 | Mcginley |
| 2,153,889 | A | 4/1939 | Hames |

(Continued)

FOREIGN PATENT DOCUMENTS

| | | |
|---|---|---|
| CA | 1317836 C | 5/1993 |
| CN | 101489502 A | 7/2009 |

(Continued)

OTHER PUBLICATIONS

"A Basic Explanation of Grain Lines," Fabrics and Textiles, Patternmaking, Sewing and Construction; Feb. 11, 2011 (https://www.thecuttingclass.com/grainlines) (Year: 2011).
(Continued)

*Primary Examiner* — Ashley L Fishback
(74) *Attorney, Agent, or Firm* — Weber Rosselli & Cannon LLP

(57) ABSTRACT

The present invention relates to a prosthesis (200) comprising: —one mesh (1) delimited by a peripheral exterior edge (1a), —a frame (2) fastened to said mesh and adopting the shape of said peripheral exterior edge of the mesh, said frame being set back from said peripheral exterior edge and being provided with two hinge points (3a, 3b), the line passing through said two hinge points also passing through the centre (1b) of the mesh and thus forming a line M for folding the mesh in two, characterized in that said prosthesis further comprises at least two anchor pieces (5) made of suturable material and located on a single face of the mesh (1) on either side of said folding line, each piece having a fixed part (5a) linked to said mesh and a free part (5b), said free part being linked to at least one thread-shaped element (7).

20 Claims, 10 Drawing Sheets

Figure 1:
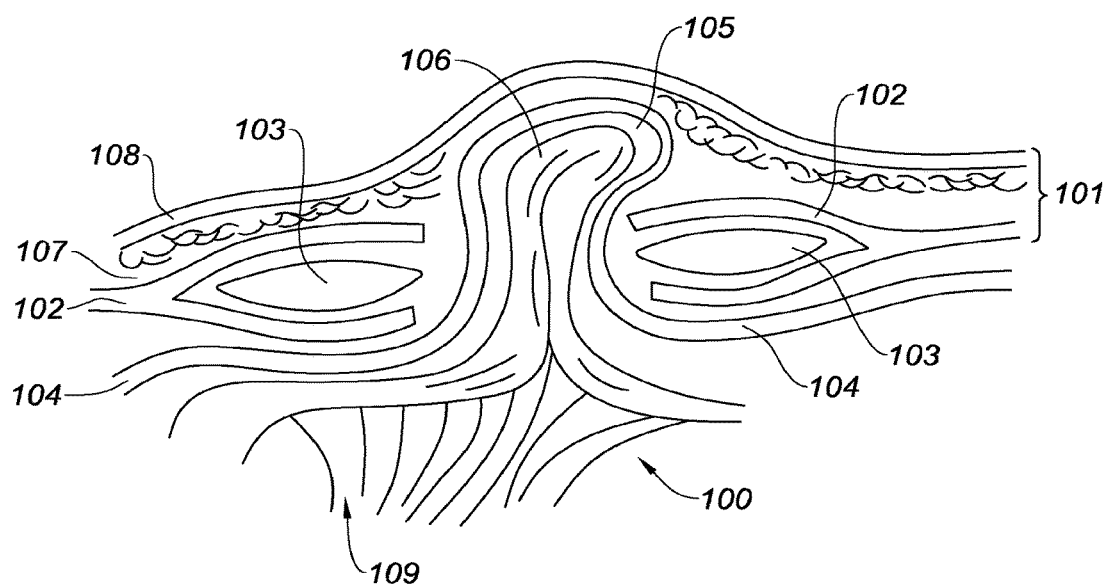

Related U.S. Application Data continuation of application No. 15/963,523, filed on Apr. 26, 2018, now Pat. No. 10,709,538, which is a continuation of application No. 14/232,378, filed as application No. PCT/EP2012/062672 on Jun. 29, 2012, now Pat. No. 9,980,802.

(51) Int. Cl.
  *A61B 17/04* (2006.01)
  *A61B 17/06* (2006.01)

(52) U.S. Cl.
  CPC ..... *A61B 17/06* (2013.01); *A61B 2017/00597* (2013.01); *A61B 2017/00623* (2013.01); *A61B 2017/0496* (2013.01); *A61F 2210/0014* (2013.01); *A61F 2210/0076* (2013.01); *A61F 2220/0008* (2013.01); *A61F 2250/0031* (2013.01); *F04C 2270/041* (2013.01)

(56) References Cited

U.S. PATENT DOCUMENTS

| | | |
|---|---|---|
| 3,054,406 A | 9/1962 | Usher |
| 3,118,294 A | 1/1964 | Van Laethem |
| 3,124,136 A | 3/1964 | Usher |
| 3,272,204 A | 9/1966 | Artandi et al. |
| 3,276,448 A | 10/1966 | Kronenthal |
| 3,320,649 A | 5/1967 | Naimer |
| 3,364,200 A | 1/1968 | Ashton et al. |
| 3,570,482 A | 3/1971 | Shigeru et al. |
| 3,718,725 A | 2/1973 | Hamano |
| 4,006,747 A | 2/1977 | Kronenthal et al. |
| 4,060,081 A | 11/1977 | Yannas et al. |
| 4,173,131 A | 11/1979 | Melton et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 4,976,737 A | 12/1990 | Leake |
| 5,002,551 A | 3/1991 | Linsky et al. |
| 5,015,584 A | 5/1991 | Brysk |
| 5,116,357 A | 5/1992 | Eberbach |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,195,542 A | 3/1993 | Gazielly et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,258,000 A | 11/1993 | Gianturco |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | Mcmurray |
| 5,350,583 A | 9/1994 | Yoshizato et al. |
| 5,356,432 A | 10/1994 | Rutkow et al. |
| 5,368,549 A | 11/1994 | Mcvicker |
| 5,368,602 A | 11/1994 | Torre |
| 5,370,650 A | 12/1994 | Jonathan et al. |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,676,967 A | 10/1997 | Williams et al. |
| 5,681,568 A | 10/1997 | Goldin et al. |
| 5,686,090 A | 11/1997 | Schilder et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,702,416 A | 12/1997 | Kieturakis et al. |
| 5,709,934 A | 1/1998 | Bell et al. |
| 5,711,960 A | 1/1998 | Shikinami |
| 5,716,409 A | 2/1998 | Debbas |
| 5,720,981 A | 2/1998 | Eisinger |
| 5,732,572 A | 3/1998 | Litton |
| 5,743,917 A | 4/1998 | Saxon |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |

(56) References Cited

U.S. PATENT DOCUMENTS

| | | |
|---|---|---|
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | Mcgregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Robert |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,090,116 A | 7/2000 | D Aversa et al. |
| 6,113,623 A | 9/2000 | Sgro |
| 6,120,539 A | 9/2000 | Eldridge et al. |
| 6,132,765 A | 10/2000 | Dicosmo et al. |
| 6,143,037 A | 11/2000 | Goldstein et al. |
| 6,153,292 A | 11/2000 | Bell et al. |
| 6,162,962 A | 12/2000 | Hinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,180,848 B1 | 1/2001 | Flament et al. |
| 6,197,325 B1 | 3/2001 | Macphee et al. |
| 6,197,934 B1 | 3/2001 | Devore et al. |
| 6,197,935 B1 | 3/2001 | Doillon et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,306,424 B1 | 10/2001 | Vyakamam et al. |
| 6,312,474 B1 | 11/2001 | Francis et al. |
| 6,319,264 B1 | 11/2001 | Tormala et al. |
| 6,328,686 B1 | 12/2001 | Robert |
| 6,334,872 B1 | 1/2002 | Termin et al. |
| 6,371,975 B2 | 4/2002 | Cruise et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | Devore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,458,889 B1 | 10/2002 | Trollsas et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Mueller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,670,018 B2 | 12/2003 | Fujita et al. |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Bryan et al. |
| 6,723,335 B1 | 4/2004 | Moehlenbruck et al. |
| 6,726,660 B2 | 4/2004 | Hessel et al. |
| 6,730,299 B1 | 5/2004 | Tayot et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,743,435 B2 | 6/2004 | Devore et al. |
| 6,746,458 B1 | 6/2004 | Cloud |
| 6,752,834 B2 | 6/2004 | Geistlich et al. |
| 6,755,868 B2 | 6/2004 | Rousseau |
| 6,773,723 B1 | 8/2004 | Spiro et al. |

(56) References Cited

U.S. PATENT DOCUMENTS

| | | |
|---|---|---|
| 6,783,554 B2 | 8/2004 | Amara et al. |
| 6,790,213 B2 | 9/2004 | Cherok et al. |
| 6,790,454 B1 | 9/2004 | Abdul et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,380 B2 | 3/2010 | Cauthen, III et al. |
| 7,682,381 B2 | 3/2010 | Rakos et al. |
| 7,709,017 B2 | 5/2010 | Tayot et al. |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,900,484 B2 | 3/2011 | Cherok et al. |
| 7,931,695 B2 | 4/2011 | Ringeisen |
| 8,048,441 B2 | 11/2011 | Craig et al. |
| 8,052,759 B2 | 11/2011 | Dupic et al. |
| 8,079,023 B2 | 12/2011 | Chen |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,435,307 B2 | 5/2013 | Paul |
| 8,470,355 B2 | 6/2013 | Skalla et al. |
| 8,562,633 B2 | 10/2013 | Cully et al. |
| 8,574,627 B2 | 11/2013 | Martakos et al. |
| 8,709,094 B2 | 4/2014 | Stad et al. |
| 8,734,471 B2 | 5/2014 | Deitch |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,911,504 B2 | 12/2014 | Mathisen et al. |
| 8,920,370 B2 | 12/2014 | Sholev et al. |
| 8,945,663 B2 | 2/2015 | Pacetti |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 9,034,357 B2 | 5/2015 | Stopek |
| 9,113,993 B2 | 8/2015 | Lee |
| 9,211,175 B2 | 12/2015 | Stopek et al. |
| 9,216,075 B2 | 12/2015 | Bailly et al. |
| 9,980,802 B2 | 5/2018 | Bailly et al. |
| 2002/0077661 A1 | 6/2002 | Saadat |
| 2002/0087174 A1 | 7/2002 | Capello |
| 2002/0095218 A1 | 7/2002 | Carr et al. |
| 2003/0086975 A1 | 5/2003 | Ringeisen |
| 2003/0114937 A1 | 6/2003 | Leatherbury et al. |
| 2003/0133967 A1 | 7/2003 | Ruszczak et al. |
| 2003/0225355 A1 | 12/2003 | Butler |
| 2004/0019360 A1 | 1/2004 | Farnsworth et al. |
| 2004/0034373 A1 | 2/2004 | Schuldt-Hempe et al. |
| 2004/0054376 A1 | 3/2004 | Ory et al. |
| 2004/0059356 A1 | 3/2004 | Gingras |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0064175 A1 | 3/2006 | Pelissier et al. |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0195010 A1 | 8/2006 | Arnal et al. |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0088391 A1 | 4/2007 | Mcalexander et al. |
| 2007/0129736 A1 | 6/2007 | Solecki |
| 2007/0198040 A1 | 8/2007 | Buevich et al. |
| 2007/0299538 A1 | 12/2007 | Roeber |
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0147099 A1 | 6/2008 | Uen |
| 2008/0147200 A1 | 6/2008 | Rousseau et al. |
| 2008/0172071 A1 | 7/2008 | Barker |
| 2008/0255593 A1 | 10/2008 | St-Germain |
| 2009/0035341 A1 | 2/2009 | Wagener et al. |
| 2009/0036996 A1 | 2/2009 | Roeber |
| 2009/0068250 A1 | 3/2009 | Gravagna et al. |

(56) References Cited

U.S. PATENT DOCUMENTS

| | | |
|---|---|---|
| 2009/0105526 A1 | 4/2009 | Piroli et al. |
| 2009/0163936 A1 | 6/2009 | Yang et al. |
| 2009/0187197 A1 | 7/2009 | Roeber et al. |
| 2009/0192530 A1 | 7/2009 | Adzich et al. |
| 2009/0204129 A1 | 8/2009 | Fronio |
| 2009/0216338 A1 | 8/2009 | Gingras et al. |
| 2009/0270999 A1 | 10/2009 | Brown |
| 2009/0281558 A1 | 11/2009 | Li et al. |
| 2009/0318752 A1 | 12/2009 | Evans et al. |
| 2010/0104608 A1 | 4/2010 | Abuzaina et al. |
| 2010/0241145 A1* | 9/2010 | Cook .................. A61F 2/0063 606/228 |
| 2010/0318108 A1 | 12/2010 | Datta et al. |
| 2011/0015760 A1 | 1/2011 | Kullas |
| 2011/0144667 A1 | 6/2011 | Horton et al. |
| 2011/0178538 A1* | 7/2011 | Cook .................. A61F 2/0063 606/151 |
| 2011/0190795 A1 | 8/2011 | Hotter et al. |
| 2011/0236460 A1 | 9/2011 | Stopek et al. |
| 2011/0238094 A1 | 9/2011 | Thomas et al. |
| 2011/0251699 A1 | 10/2011 | Ladet et al. |
| 2011/0257666 A1 | 10/2011 | Ladet et al. |
| 2011/0266778 A1 | 11/2011 | Jakobsson |
| 2012/0016388 A1 | 1/2012 | Houard et al. |
| 2012/0029537 A1 | 2/2012 | Mortarino |
| 2012/0065727 A1 | 3/2012 | Reneker et al. |
| 2012/0082712 A1 | 4/2012 | Stopek et al. |
| 2012/0116425 A1 | 5/2012 | Intoccia et al. |
| 2012/0150204 A1 | 6/2012 | Mortarino et al. |
| 2012/0165937 A1 | 6/2012 | Montanari et al. |
| 2012/0179175 A1 | 7/2012 | Hammell et al. |
| 2012/0179176 A1 | 7/2012 | Wilson et al. |
| 2012/0197415 A1 | 8/2012 | Montanari et al. |
| 2014/0044861 A1 | 2/2014 | Boey et al. |
| 2014/0364684 A1 | 12/2014 | Lecuivre et al. |

FOREIGN PATENT DOCUMENTS

| | | |
|---|---|---|
| CN | 201879864 U | 6/2011 |
| DE | 19544162 C1 | 4/1997 |
| DE | 19718903 A1 | 12/1997 |
| DE | 19636961 A1 | 3/1998 |
| DE | 19751733 A1 | 12/1998 |
| DE | 19832634 A1 | 1/2000 |
| DE | 10019604 A1 | 10/2001 |
| DE | 10120942 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 0544485 A1 | 6/1993 |
| EP | 0552576 A1 | 7/1993 |
| EP | 0611561 A1 | 8/1994 |
| EP | 0614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 0827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 0898944 A2 | 3/1999 |
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1216717 A1 | 6/2002 |
| EP | 1216718 A1 | 6/2002 |
| EP | 0693523 B1 | 11/2002 |
| EP | 1273312 A2 | 1/2003 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1674048 A1 | 6/2006 |
| EP | 1691606 A1 | 8/2006 |
| EP | 1782848 A2 | 5/2007 |
| EP | 2229918 A1 | 9/2010 |
| FR | 2244853 A1 | 4/1975 |
| FR | 2257262 A1 | 8/1975 |
| FR | 2308349 A1 | 11/1976 |
| FR | 2453231 A1 | 10/1980 |
| FR | 2612392 A1 | 9/1988 |
| FR | 2715309 A1 | 7/1995 |
| FR | 2715405 A1 | 7/1995 |
| FR | 2724563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2859624 B1 | 12/2005 |
| FR | 2876020 A1 | 4/2006 |
| FR | 2863277 B1 | 6/2006 |
| FR | 2884706 B1 | 4/2008 |
| FR | 2929834 A1 | 10/2009 |
| FR | 2951069 A1 | 4/2011 |
| FR | 2953709 A1 | 6/2011 |
| GB | 1174814 A | 12/1969 |
| GB | 2051153 A | 1/1981 |
| GB | 2306110 A | 4/1997 |
| JP | H0332677 U | 3/1991 |
| JP | H05237128 A | 9/1993 |
| JP | H09137380 A | 5/1997 |
| JP | H11146888 A | 6/1999 |
| JP | 2008538300 A | 10/2008 |
| JP | 2010508121 A | 3/2010 |
| JP | 2011078767 A | 4/2011 |
| WO | 8902445 A1 | 3/1989 |
| WO | 8908467 A1 | 9/1989 |
| WO | 9012551 A1 | 11/1990 |
| WO | 9206639 A2 | 4/1992 |
| WO | 9220349 A1 | 11/1992 |
| WO | 9307321 A1 | 4/1993 |
| WO | 9311805 A1 | 6/1993 |
| WO | 9318174 A1 | 9/1993 |
| WO | 9417747 A1 | 8/1994 |
| WO | 9507666 A1 | 3/1995 |
| WO | 9518638 A1 | 7/1995 |
| WO | 9532687 A1 | 12/1995 |
| WO | 9603091 A1 | 2/1996 |
| WO | 9608277 A1 | 3/1996 |
| WO | 9609795 A1 | 4/1996 |
| WO | 9614805 A1 | 5/1996 |
| WO | 9641588 A1 | 12/1996 |
| WO | 9735533 A1 | 10/1997 |
| WO | 9831345 A1 | 7/1998 |
| WO | 9835632 A1 | 8/1998 |
| WO | 9849967 A1 | 11/1998 |
| WO | 9905990 A1 | 2/1999 |
| WO | 9906079 A1 | 2/1999 |
| WO | 9906080 A1 | 2/1999 |
| WO | 9951163 A1 | 10/1999 |
| WO | 0016821 A1 | 3/2000 |
| WO | 0067663 A1 | 11/2000 |
| WO | 0115625 A1 | 3/2001 |
| WO | 0180773 A1 | 11/2001 |
| WO | 0181667 A1 | 11/2001 |
| WO | 0207648 A1 | 1/2002 |

(56) References Cited

FOREIGN PATENT DOCUMENTS

| WO | 0217853 A2 | 3/2002 |
|---|---|---|
| WO | 02078568 A1 | 10/2002 |
| WO | 03002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 2005011280 A1 | 2/2005 |
| WO | 2005013863 A2 | 2/2005 |
| WO | 2005018698 A1 | 3/2005 |
| WO | 2005048708 A1 | 6/2005 |
| WO | 2005105172 A1 | 11/2005 |
| WO | 2006018552 A1 | 2/2006 |
| WO | 2006023444 A2 | 3/2006 |
| WO | 2006040760 A2 | 4/2006 |
| WO | 2009071998 A2 | 6/2009 |
| WO | 2009031035 A3 | 1/2010 |
| WO | 2010043978 A2 | 4/2010 |
| WO | 2010043980 A2 | 4/2010 |
| WO | 2007048099 A3 | 9/2010 |
| WO | 2011007062 A1 | 1/2011 |
| WO | 2011026987 A1 | 3/2011 |
| WO | 2011038740 A1 | 4/2011 |

OTHER PUBLICATIONS

Amid, P., "Lichtenstein tension-free hernioplasty: Its inception, evolution, and principles," Hernia, 2004; pp. 1-7, 8, published online Sep. 2003.

Blondin, C. et al., "Inhibition of Complement Activation by Natural Sulfated Polysaccharides (Fucans) from Brown Seaweed," Molecular Immuol., Mar. 1994, pp. 247-253, 31(4).

Blondin, C. et al., "Relationships between chemical characteristics and anticomplementary activity of fucans," Biomaterials, Mar. 1996, pp. 597-603, 17(6).

Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Chen, G. et al., "A Hybrid Network of Synthetic Polymer Mesh and Collagen Sponge," The Royal Society of Chemistry 2000, Chem. Commun., Jul. 2000, pp. 1505-1506.

Collins, R. et al., "Use of collagen film as a dural substitute: Preliminary animal studies," Journal of Biomedical Materials Research, Feb. 1991, pp. 267-276, vol. 25.

Dr. S. Raz, "The Karl Mayer Guide to Tehnical Textiles," Jan. 2000, pp. 1-36, Obertshausen, Germany.

Haneji, K et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.

Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).

Haroun-Bouhedja, F. et al., "Relationship between sulfate groups and biological activities of fucans," Thrombosis Res., Dec. 2000, pp. 453-459, 100(5).

Hirano, S. et al., "The blood biocompatibility of chitosan and N-acylchitosans," J. Biomed. Mater. Res., Apr. 1985, 413-417, 19.

International Search Report issued in corresponding application No. PCT/EP2012/062672, dated Sep. 4, 2012.

Japanese Office Action dated May 2, 2016 in corresponding Japanese Patent Application No. 2014-519494, together with English translation, 9 pages.

Junge, K. et al., "Functional and Morphologic Properties of a Modified Mesh for Inguinal Hernia Repair," World J. Surg., Sep. 2002, pp. 1472-1480, 26.

Kanabar, V. et al., "Some structural determinants of the antiproliferative effect of heparin-like molecules on human airway smooth muscle, " Br. J. Pharmacol., Oct. 2005, pp. 370-777, 146(3).

Klinge, U. et al., "Foreign Body Reaction to Meshes Used for the Repair of Abdominal Wall Hernias," Eur J. Surg, Sep. 1999, pp. 665-673, 165.

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.

Langenbech, M. R. et al., "Comparison of biomaterials in the early postoperative period," Surg Endosc., May 2003, pp. 1105-1109, 17 (7).

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).

Malette, W. G. et al., "Chitosan, A New Hemostatic," Ann Th. Surg., Jul. 1983, pp. 55-58, 36.

Muzzarelli, R. et al., "Reconstruction of parodontal tissue with chitosan," Biomaterials, Nov. 1989, pp. 598-604, 10.

O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).

Prokop, A. et al., "Water Soluble Polymers for Immunoisolation I: Complex Coacervation and Cytotoxicity," Advances in Polymer Science, Jul. 1998, pp. 1-51, 136.

Rao, B. et al., "Use of chitosan as a biomaterial: Studies on its safety and hemostatic potential," J. Biomed. Mater. Res., Jan. 1997, pp. 21-28, 34.

Rosen, M. et al., "Laparoscopic component separation in the single-stage treatment of infected abdominal wall prosthetic removal," Hernia, 2007, pp. 435-440, 11, published online Jul. 2007.

Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220, 18(2).

Strand, S. et al., "Screening of Chitosans and Conditions for Bacterial Flocculation," Biomacromolecules, Mar. 2001, 126-133, 2.

Varum, K. et al., "In vitro degradation rates of partially N-acetylated chitosans in human serum," Carbohydrate Research, Mar. 1997, pp. 99-101, 299.

Welty, G. et al., "Functional impairment and complaints following incisional hernia repair with different polypropylene meshes," Hernia, Aug. 2001; pp. 142-147, 5.

Zvyagintseva, T. et al., "Inhibition of complement activation by water-soluble polysaccharides of some far-eastern brown seaweeds," Comparative Biochem and Physiol, Jul. 2000, pp. 209-215, 126(3).

\* cited by examiner

UMBILICAL HERNIA PROSTHESIS

CROSS-REFERENCE TO RELATED APPLICATIONS

This application is a divisional application of U.S. patent application Ser. No. 16/927,735 filed Jul. 13, 2020, which is a continuation of U.S. patent application Ser. No. 15/963,523 filed Apr. 26, 2018, now U.S. Pat. No. 10,709,538, which is a continuation application of U.S. patent application Ser. No. 14/232,378 filed Mar. 24, 2014, now U.S. Pat. No. 9,980,802, which is a National Stage Application of PCT/EP2012062672 filed Jun. 29, 2012, which claims benefit of and priority to French Patent Application No. 11/56425 filed Jul. 13, 2011, the disclosures of each of the above-identified applications are hereby incorporated by reference in their entirety.

The present invention provides a prosthesis, for repairing hernias, for example, comprising a mesh and a member for reinforcing the mesh.

In humans the abdominal wall consists of fat and muscles interconnected by aponeuroses. A break in continuity may occur at the level of the aponeuroses, allowing part of the peritoneum to pass through and form a sac, known as a hernia, containing either fat or a portion of the intestine. Hernias or ventral ruptures (hernias occurring on a parietal surgical scar) are manifested by a protrusion on the surface of the skin and are called umbilical or inguinal hernias or ventral ruptures, for example, as a function of their location.

To repair a hernia, surgeons often fit a synthetic mesh prosthesis that replaces or reinforces the weakened anatomical tissue.

However, the efficacy of the prosthesis, and thus minimizing the risk of relapse, depend to a great degree on the proper fixing of the prosthesis. In particular, before being fixed, the prosthesis must be correctly spread over the abdominal wall that it is intended to reinforce. Prostheses of mesh type, i.e. based on an arrangement of threads forming a textile, are generally flexible, and to introduce them into the hernia they are often folded to reduce their volume. They therefore tend to form creases on the abdominal wall when they are introduced onto the implantation site. In this respect spreading them out is of primary importance but may prove difficult, in particular in the case of treating an umbilical hernia, which, being smaller than an inguinal hernia, offers little working space and little visibility for manipulation of the prosthesis by the surgeon.

In the case of umbilical hernias, for example, or when the aim of treatment is to repair trocart holes or preventive, the size of the defect to be treated is small, for example from 1 to 4 cm diameter, and open surgery may be envisaged without widening the defect. However, in this type of surgery, the surgeon has little working space and little visibility. It would thus be preferable to have a prosthesis that is easy to position, to spread out and to fix, if possible avoiding the necessity for sutures at the periphery of the prosthesis, which is complicated and laborious under such working conditions.

Failure to spread the prosthesis out perfectly against the abdominal wall leads to the risk of trapping the peritoneal sac and the risk of insertion of a soft organ between the prosthesis and the abdominal wall, which can lead to the risk of adhesions, pain and intestinal blockage and increase the possibility of relapse. It is therefore essential for the surgeon to be sure that no part of the prosthesis remains folded and that no viscera or any part of the intestines lie between the prosthesis and the abdominal wall. Moreover, incorrect positioning of the sutures or incorrect fixing of the prosthesis risks distortion of the prosthesis and the creation of tensions.

Thus in the case of an umbilical hernia in particular, having a small orifice for introducing the prosthesis, it would be beneficial to have a prosthesis adapted to occupy a small volume in a first configuration in order to facilitate its introduction into the abdominal cavity via said orifice and then to be deployed, spread out and pressed easily against the abdominal wall so that the surgeon is sure of the optimal positioning of the prosthesis and can moreover fix the prosthesis efficaciously without sutures at its periphery, and this, despite the little intrinsic visibility of small size hernias.

Various prostheses that may be folded up and then deployed are available.

The present invention concerns a prosthesis that is adapted to be folded up in order to reduce the volume that it occupies at the time of its introduction into a small incision and on the other hand to be spread out and fixed easily so that the surgeon is sure of the perfect spreading of the prosthesis and that it may be fixed efficaciously at a certain distance between the centre of the prosthesis and its periphery without sutures at the periphery of the prosthesis and this, despite the little intrinsic visibility of small size hernias.

The prosthesis of the invention is beneficial for treating hernias of the abdominal wall, in particular for treating umbilical hernias where the defect is small.

A first aspect of the present invention provides a prosthesis comprising:
- at least one flexible mesh delimited by a peripheral exterior edge,
- at least one member for reinforcing said mesh, said reinforcing member taking the form of a frame fastened to said mesh and substantially adopting the shape of said peripheral exterior edge of the mesh, said frame being set back from said peripheral exterior edge and being provided with two hinge points, the line passing through said two hinge points also passing through the centre of the mesh and thus forming a line M for folding the mesh in two,
- characterized in that said prosthesis further comprises at least two anchor pieces made of suturable material and located on a single face of the mesh on either side of said folding line, each piece having a fixed part linked to said mesh and a free part, said free part being linked to at least one thread-shaped element.

The reinforcing member or frame may be rigid or have some flexibility. According to the present invention, the mesh and thus the prosthesis can be folded in two because of the presence of the two hinge points of the frame, regardless of the presence or not of intrinsic elastic properties of the frame.

In the context of the present application the term "mesh" refers to an arrangement of biocompatible threads, for example a knitted, woven or non-woven material, preferably of the openwork kind, i.e. having pores encouraging tissue recolonization. Such a mesh may be bioresorbable, partly bioresorbable or permanent. It is sufficiently flexible to be folded up at the time of its introduction into the abdominal cavity. The mesh may be produced from one layer of textile or from a plurality of layers of textiles. Such meshes are well known to the person skilled in the art. The mesh usable for the invention may be supplied in any shape (rectangular, square, circular, oval, etc.) and then cut to match the shape of the hernia defect. For example, the mesh may have the overall shape of a disc or an oval: in this case the frame also has a circular or oval shape and is preferably in the form of a ring. Alternatively, the mesh may have a globally square or rectangular shape: in this case the frame also has a square or rectangular shape. The frame is set back from the exterior peripheral edge of the mesh: thus, whilst adopting the shape of the contour of the mesh, the frame has an exterior perimeter smaller than that of the exterior peripheral edge of the mesh: in other words, the exterior peripheral edge of the mesh extends a certain distance beyond the frame. This distance may be greater than or equal to 1 mm, for example. In other words also, the frame and the exterior peripheral edge of the mesh are of similar geometric shape but the frame shows dimensions which are less than that of the exterior peripheral edge of the mesh.

As will become apparent from the following description, the shape of the frame and its location, set back slightly from the exterior peripheral edge of the mesh, enable the surgeon, when implanting the prosthesis, to fix it to the peritoneum efficaciously without requiring sutures at the periphery of the mesh: the surgeon is able to fix the prosthesis along the interior contour of the frame only, said interior contour defining a stitches fixing line: this avoids the surgeon having to apply stitches to the prosthesis at the exterior peripheral edge of the mesh, which is difficult to reach and hardly visible because of the small size of the incision. The interior contour of the frame of the prosthesis of the invention defines a fixing line, or stitching line, located approximately half way between the centre of the mesh and its exterior peripheral edge, along which the surgeon may locate the stitches when he fixes the prosthesis to the abdominal wall. Nevertheless, perfect spreading out of the prosthesis is assured by the presence of the frame which, by adopting the shape of the contour of the exterior peripheral edge, ensures deployment of the prosthesis and pressing thereof onto the abdominal wall.

In the context of the present application, by "anchor piece made of suturable material" is meant that the anchor piece is capable of being linked to, or passed through by, a thread-shaped element as defined in the present application, without being torn off when a user, such as a surgeon for example, exerts a moderate tension on said thread-shaped element, such as the necessary tension for orientating and/or positioning the prosthesis in the implantation site, as described hereinafter. Thus the anchor piece may be under the form of a textile, either knitted, woven or nonwoven, open worked or not; alternatively or in addition, the anchor piece may be under the form of a film or a sheet of material, as long as this textile, film and/or sheet of material is not torn off under the effect of the moderate tension as described above exerted on a thread-shaped element linked to, or passing through, said textile, film and/or sheet.

The anchor pieces may be made of bioresorbable material or not. The bioresorbable material may be chosen, for example, from polylactic acid (PLA), polycaprolactone (PCL), polydioxanone (PDO), trimethylene carbonate (TMC), polyvinyl alcohol (PVA), polyhydroxyalkanoate (PHA), oxidized cellulose, polyglycol acid (PGA), copolymers of these materials and mixtures thereof.

As will be apparent from the following description, the anchor pieces are useful to the surgeon for facilitating the positioning of the prosthesis in the centre of the defect to be treated, and for attaching the prosthesis to the biological tissues. The anchor pieces also form the parts of the prosthesis by which said prosthesis is sutured to the abdominal wall.

The anchor pieces of the prosthesis of the invention are located on one single face of the mesh: as will be apparent from the following description, the anchor pieces are located on the face of the mesh intended to face the abdominal wall once the prosthesis is implanted: indeed, said anchor pieces are intended to be reached by the surgeon through the incision made for the implantation, in particular by means of thread-shaped elements, in view of assisting the surgeon to orientate and position the prosthesis as well as to raise the edges of the hernia defect for visualising the area to be stitched, when the prosthesis is put in place. The prosthesis of the invention thus comprises at least two anchor pieces located on either side of the folding line, preferably at two places which are symmetrical to each other with respect to this folding line: such a location of the anchor pieces enables the surgeon to expand the prosthesis optimally when it is put in place. According to the invention, the number of anchor pieces is not limited and the prosthesis may comprise 3 or 4 anchor pieces, even more. Each anchor piece shows a fixed part linked to the mesh of the prosthesis, and a free part, not attached to the mesh, and forming a type of shutter, flap or flying part. The fixed part of the anchor piece may be linked to the mesh by gluing, welding, sewing or by any biocompatible fixing means. In one embodiment, the anchor pieces are linked to the mesh via their fixed part by means of the reinforcing member.

The anchor pieces may show any geometrical shape. They may be identical or different.

In one embodiment, each anchor piece having a geometrical shape with at least one side having a length equal or greater than that of the other sides, each anchor piece is linked to the mesh by its longest side, along a direction perpendicular to the segment linking the centre of the mesh and the point of fixation of said piece in the plane of the mesh. In such an embodiment, each anchor piece being linked to the mesh by its longest side, the free part, or shutter or flap of each piece occupies only little space in the surroundings of the mesh: this enables maintaining a clear and non obstructed space around the hernia defect when the prosthesis is put in place and therefore allows the surgeon having a good visibility of the implantation site and not being impeded by the presence of useless extra elements. Such an embodiment also enables a more secure fixation of the anchor pieces to the mesh. Moreover, the positioning of the anchor pieces, i.e. along a direction perpendicular to the segment linking the centre of the mesh and the point of fixation of said piece in the plane of the mesh, allows the surgeon to position the prosthesis optimally by pulling on the thread-shaped elements linked to the anchor pieces in a centrifugal direction with respect to the hernia defect, as will be apparent in the following description.

In one embodiment, the suturable material is a textile and the anchor pieces are textile pieces. This textile may be identical to that of the mesh, or different. For example, the anchor pieces may be sewn to the mesh.

In the context of the present application, by "thread-shaped element", is meant a flexible and elongated element, the length of which is much more greater than its thickness and its width, the contour of the cross section of which is globally circular: examples of thread-shaped elements of the invention may be a thread on its own, composite or not, or several threads, for example arranged together to make a braid, a tube, and combinations thereof. In embodiments, the thread-shaped elements are selected from threads, flexible tubes and combinations thereof.

In the prosthesis of the invention, the free part of each anchor piece is linked to at least one thread-shaped element. As will be apparent from the detailed description below, the thread-shaped element is intended to allow the surgeon to pull on the anchor piece linked thereto in order to expand, orientate and position the prosthesis when said prosthesis is put in place: preferably, the surgeon will pull simultaneously on the thread-shaped elements of the at least two anchor pieces which are present in order to counterbalance the prosthesis with respect to the defect to be treated. In addition, due to its structure, the thread-shaped element does not unnecessarily encumber the working area for the surgeon, said area being already naturally particularly limited regarding small size hernias.

In embodiments, the thread-shaped elements are flexible tubes: because of their hollow structure, necessitating a certain outer diameter, for example equal or greater than 3 mm, the tubes show a quite important outer surface capable of being in contact with the margins of the defect, this allowing decreasing dramatically the potential traumatic effect due to the contact of the tubes with the margins of the defect. The flexibility of the tubes allows their easy handling with no risk of damaging the tissues. Preferably, the tubes are flexible and semi-rigid. As will appear from the following description, such a semi-rigidity of the tubes allows maintaining the anchor pieces to which they are linked under slight tension, without having to apply any particular tension on these tubes. The flexible tubes may be in plastic material, silicone, or a combination of these materials.

In one embodiment of the invention, the mesh of the prosthesis of the invention is a knitted fabric: because of the stitches that form it, a knitted fabric makes it possible to obtain openwork faces encouraging cellular recolonization after implantation. The knitted fabric may be a two-dimensional knitted fabric or a three-dimensional knitted fabric.

In the context of the present application, the expression "two-dimensional knitted fabric" means a knitted fabric having two opposite faces linked together by stitches but having no spacers imparting a certain thickness to it: such a knitted fabric may be obtained, for example, by knitting threads on a warp or Raschel knitting machine using two guide bars. Examples of two-dimensional knitted fabrics suitable for the present invention are given in the document WO2009/071998.

In the present application, the expression "three-dimensional knitted fabric" means a knitted fabric having two opposite faces linked together by spacers imparting a significant thickness to the knitted fabric, said spacers consisting of connecting threads additional to the threads forming the two faces of the knitted fabric. Such a knitted fabric may be obtained, for example, using a double-bed Raschel knitting machine or warp knitting machine with a plurality of guide bars. Examples of knitting three-dimensional knitted fabrics suitable for the present invention are given in the documents WO99/05990, WO2009/031035, WO2009/071998.

In one embodiment, said frame is set back from the exterior peripheral edge of the mesh and is of serpentine shape, forming undulations. For example, said frame is in the form of a flat ribbon forming undulations substantially in the plane of said mesh. As will become apparent from the description given hereinafter, this configuration of the frame makes it possible, when fixing the prosthesis to the biological tissue, to execute a suture in the prosthesis at a given location without deforming the prosthesis as a whole during this operation; deformation of the prosthesis caused by the suture at the given location is smoothed out by the undulating frame. Thus the frame and therefore the rest of the prosthesis remain correctly positioned, and in particular remain pressed against the abdominal wall, during the fixing of the prosthesis.

In one embodiment, said reinforcing member is produced in bioresorbable material. Thus the reinforcing member fulfils its role of stiffening the prosthesis during positioning and implantation of the prosthesis and is then degraded progressively once the mesh is recolonized by the surrounding cells.

The bioresorbable material may be chosen, for example, from polylactic acid (PLA), polycaprolactone (PCL), polydioxanone (PDO), trimethylene carbonate (TMC), polyvinyl alcohol (PVA), polyhydroxyalkanoate (PHA), oxidized cellulose, polyglycol acid (PGA), copolymers of these materials and mixtures thereof.

Alternatively, the reinforcing member is produced in a non-bioresorbable material chosen from polypropylene, a polyester such as polyethylene terephthalate, polyamide, silicone, polyetheretherketone (PEEK), polyaryletheretherketone (PAEK) and mixtures thereof.

In another embodiment, said reinforcing member is produced from a combination of bioresorbable material and non-bioresorbable material.

In one embodiment of the invention said mesh has the shape of a disc, said frame being substantially in the form of a circular ring. In such an embodiment, said anchor pieces may be fixed to two diametrically opposed places of an inner perimeter of said ring, said two places being spaced by 90° from each of said two hinge points. Such an embodiment enables an optimal deployment of the prosthesis by pulling in opposite directions on the respective thread-shaped elements of the two anchor pieces after the folded prosthesis has been introduced in the implantation site.

Alternatively, the prosthesis comprises four said anchor pieces distributed substantially regularly along an inner perimeter of said ring so that two anchor pieces are located on one side of the folding line and the other two anchor pieces are located on the other side of said folding line. In such an embodiment, for example, a single thread-shaped element links together the free parts of two anchor pieces located on the same side of the folding line. The total number of thread-shaped elements thus remains low and the surgeon is not impeded by the presence of extra thread-shaped elements. Moreover, the deployment and orientation step of the prosthesis is rendered easier: indeed, each thread-shaped element, because it links together the free parts of two anchor pieces located on the same side of the folding line, forms a sort of loop that the surgeon may very easily grasp and handle, in particular in view of exerting a tension on this loop: in addition, such a tension enables pulling on two anchor pieces simultaneously, at two different places of the mesh, thereby allowing optimised deployment and spreading out of the mesh and of the prosthesis.

Alternatively, a single thread-shaped element may link together the free parts of two adjacent anchor pieces located on each side of the folding line.

In embodiments, the anchor pieces have a colour different than that of the mesh. Alternatively or in addition, the thread-shaped elements have a colour different than that of the mesh and than that of the anchor pieces. Thanks to the present invention, the surgeon works in a relative non obstructed implantation site where he can see the area of the prosthesis to be attached to the abdominal wall, this area being located more or less in the middle between the centre of the mesh and the edge of the mesh: such embodiments of the prosthesis of the invention allow the surgeon to easily and rapidly make the necessary stitches by enabling him, thanks to the different colours, to quickly identify whether he handles the mesh, the anchor pieces or the thread-shaped elements.

In one embodiment of the invention, the face of the mesh opposite that including said anchor pieces is covered with a non-adherent coating.

Such a coating makes it possible in particular to avoid the formation of unwanted severe post-operative fibrous adhesions.

In the context of the present application the expression "non-adherent" refers to a non-porous, smooth, biocompatible coating or material offering no space for cellular recolonization and preferably encouraging the birth of a peritoneum.

In embodiments, where the prosthesis comprises four said anchor pieces distributed substantially regularly along an inner perimeter of said ring so that two anchor pieces are located on one side of the folding line and the other two anchor pieces are located on the other side of said folding line, all four anchor pieces are under the form of isosceles triangles of textile, each triangle being fixed to said mesh via its base, all four triangles showing identical elongation and tensile strength properties in the centripetal direction.

For example, each isosceles triangle is fixed to the mesh via its base by means of the ring, the thread-shaped element being attached to the vertex angle of the isosceles triangle. Because of the four isosceles triangles of textile having the same mechanical properties in the centripetal direction, when the surgeon pulls on the thread-shaped elements at the time he puts the prosthesis in place and fixes it to the abdominal wall, all anchor pieces react similarly and the traction exerted by the surgeon on the whole prosthesis via the thread-shaped elements is regularly distributed. The prosthesis is therefore properly positioned. In addition, in embodiments where the four isosceles triangles of textile have a colour different from that of the mesh, the surgeon readily identifies the stitching line as defined above and the step of fixing the prosthesis to the abdominal wall is facilitated. As will appear from the description below, the method of manufacturing a prosthesis with four anchor pieces under the form of four isosceles triangle of textile having identical mechanical properties is simple and easy.

Figure 2:
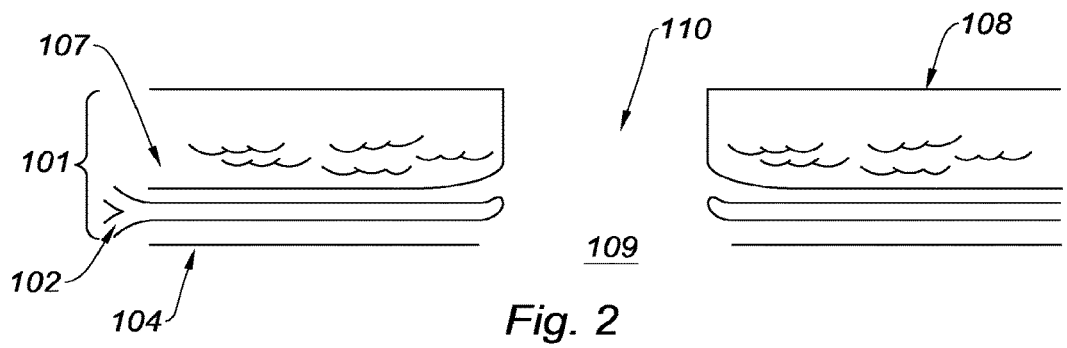
Figure 3:
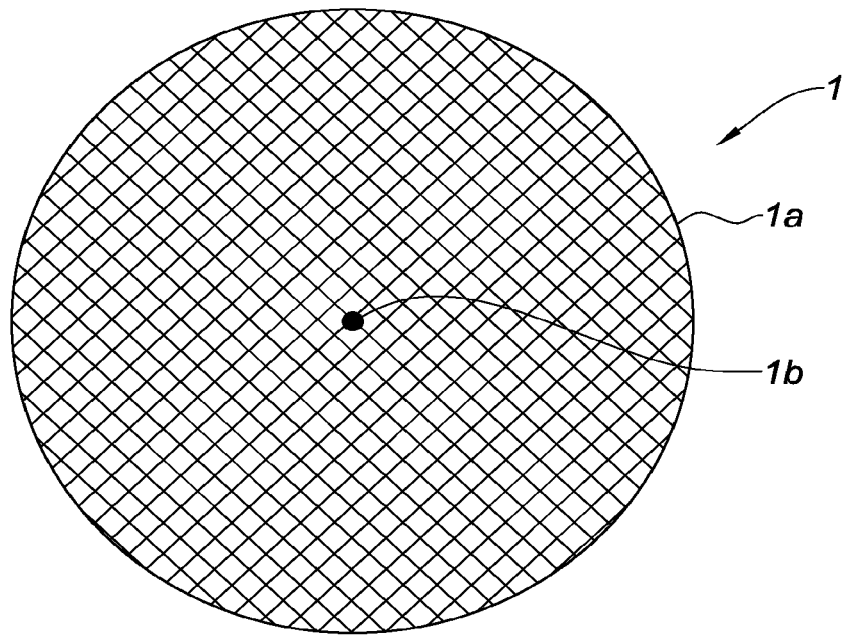
Figure 4:
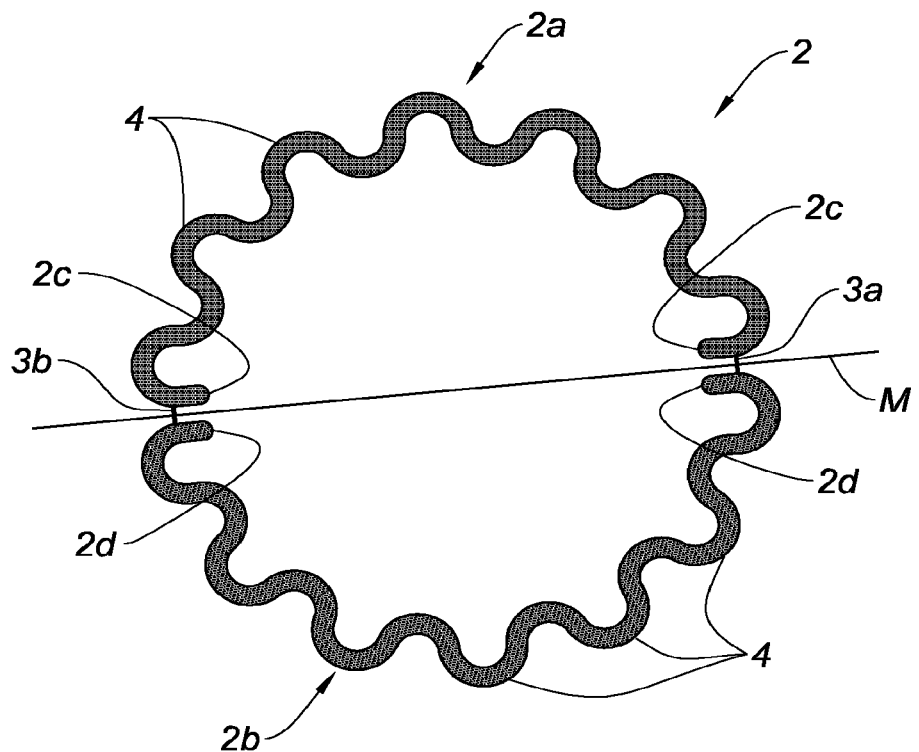
Figures 5A, 5B, 5C, 5D:
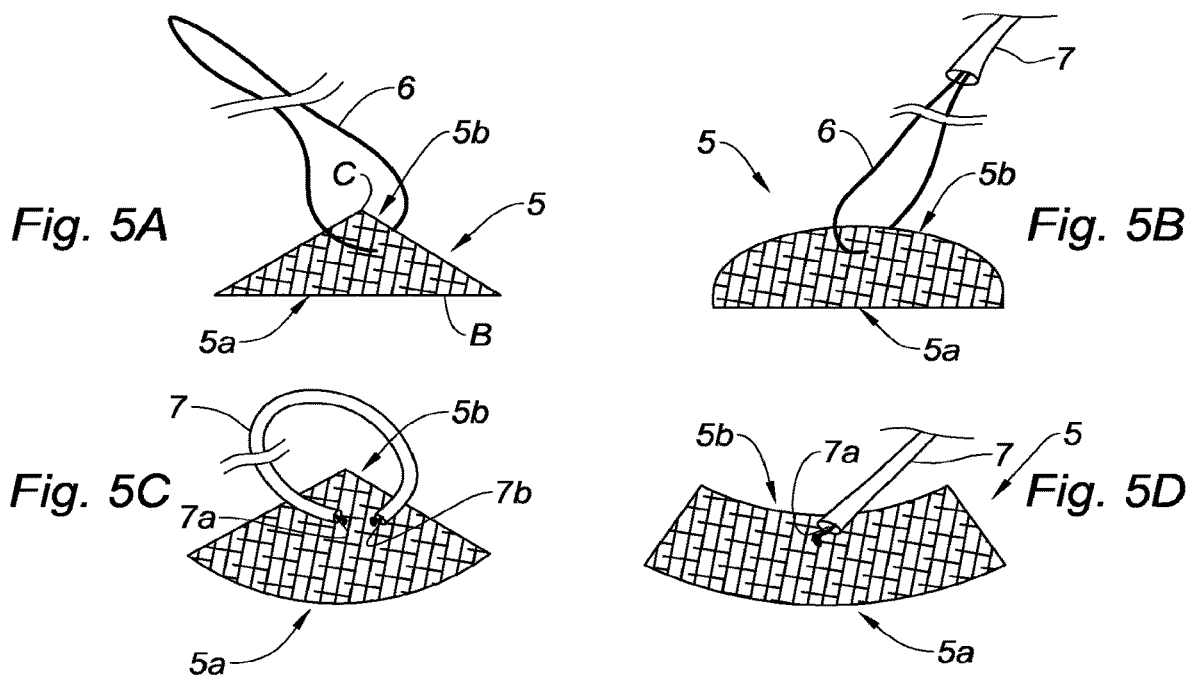
Figure 6:
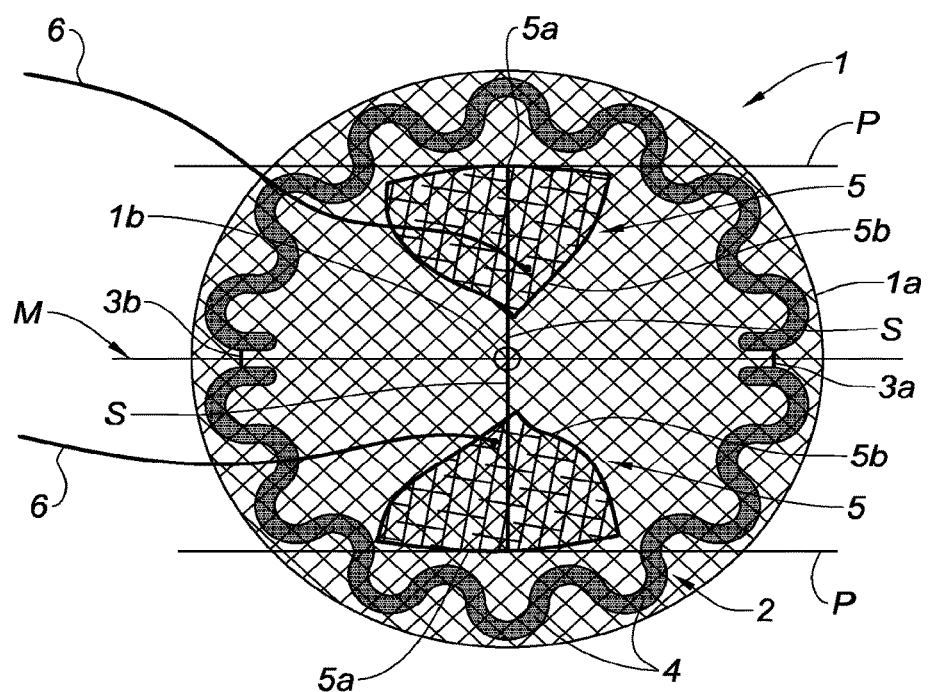
Figure 7:
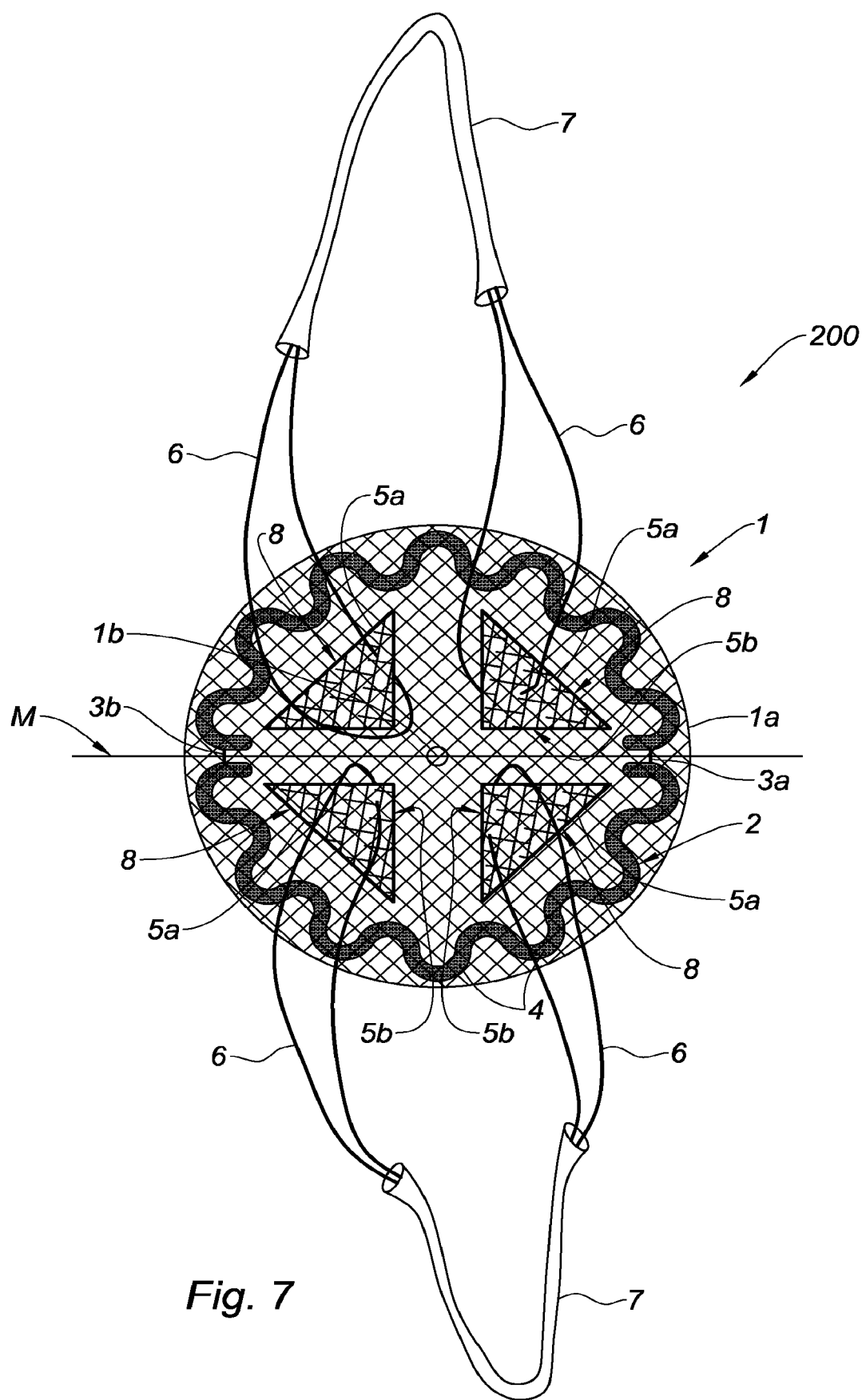
Figure 8:
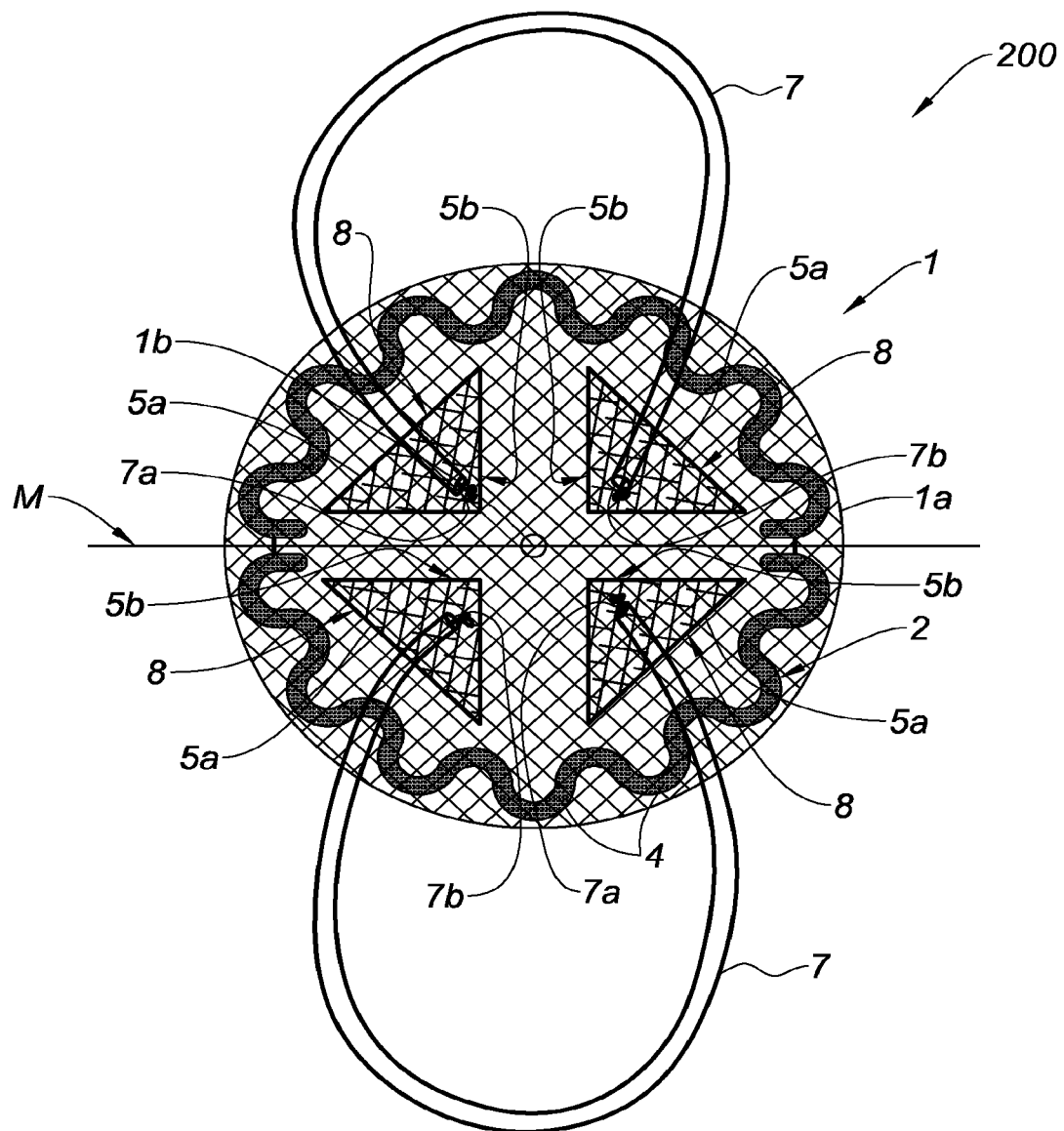
Figure 9:
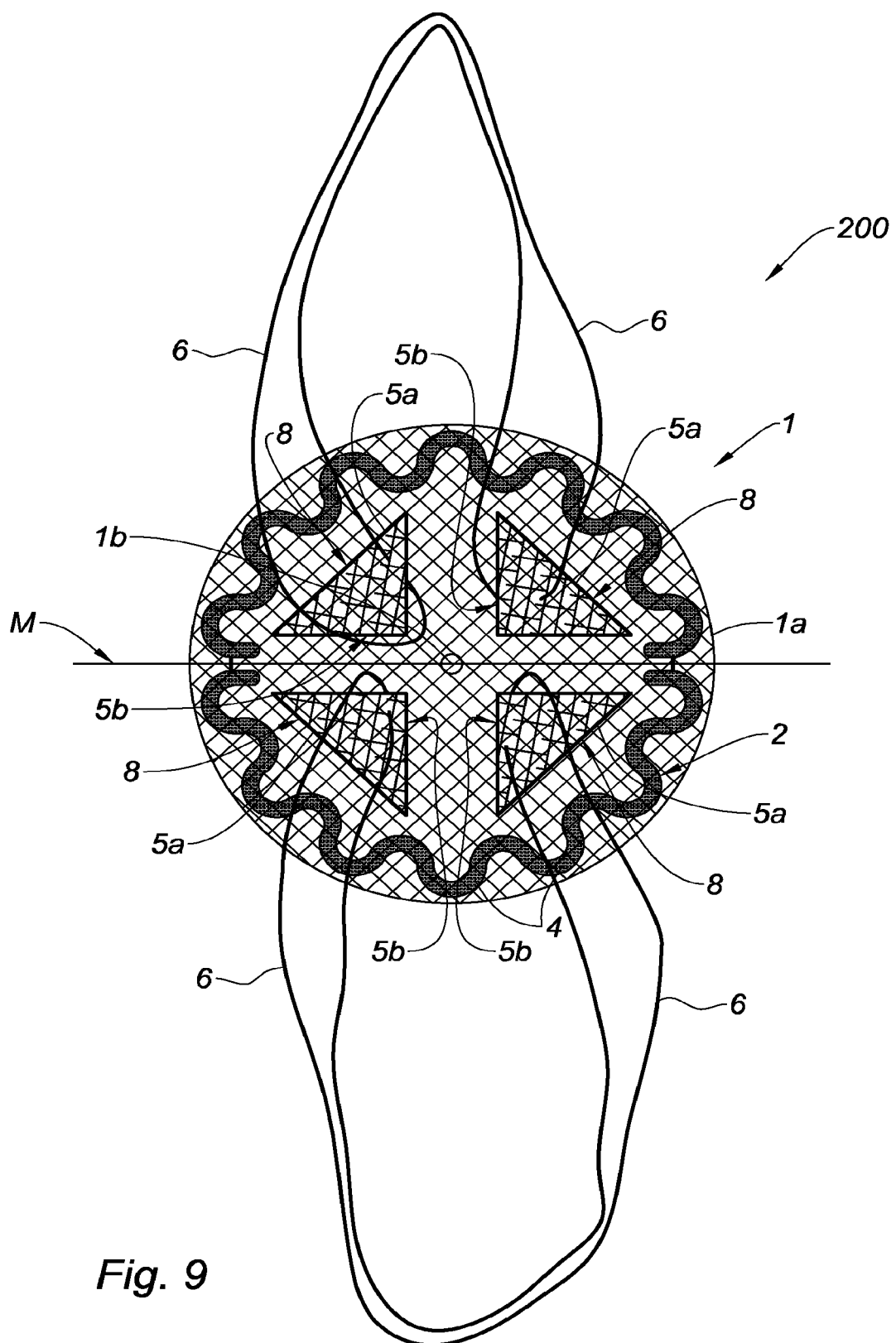
Figure 10:
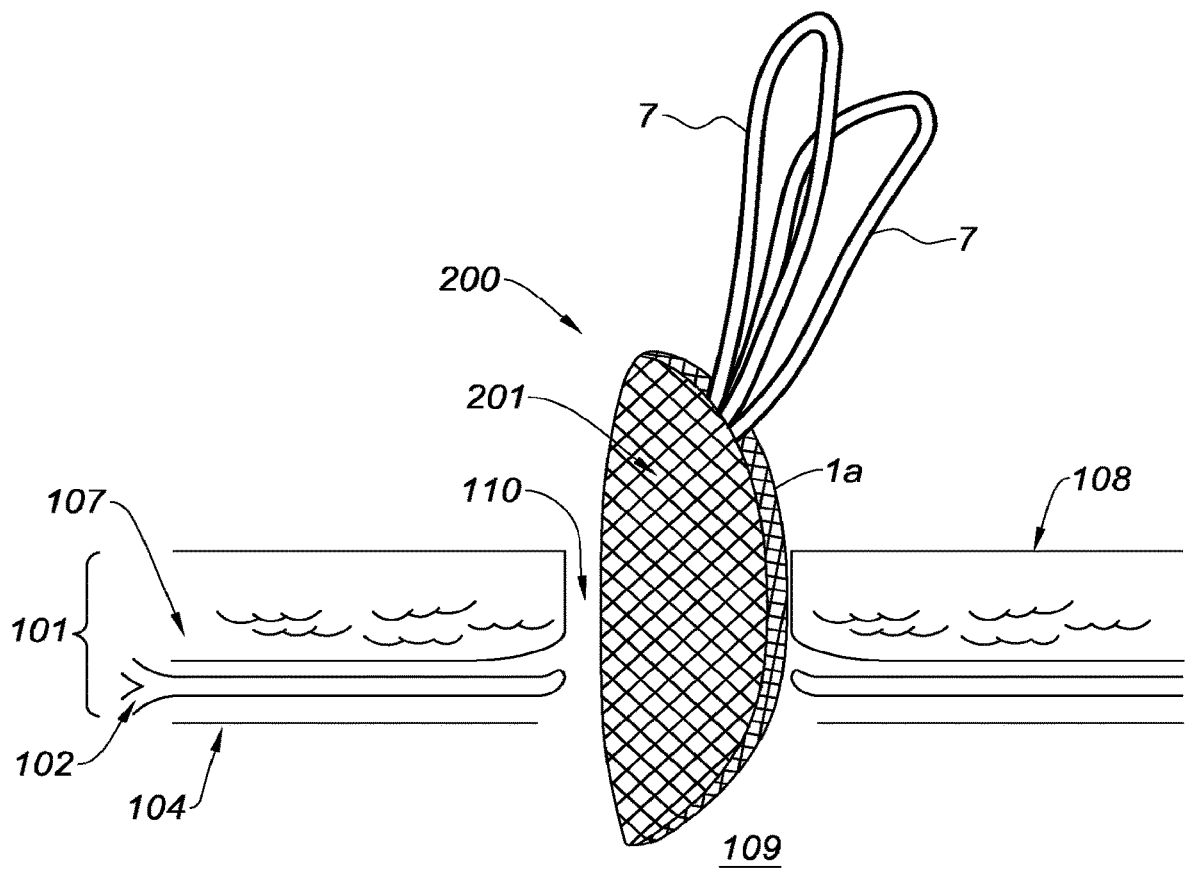
Figure 11:
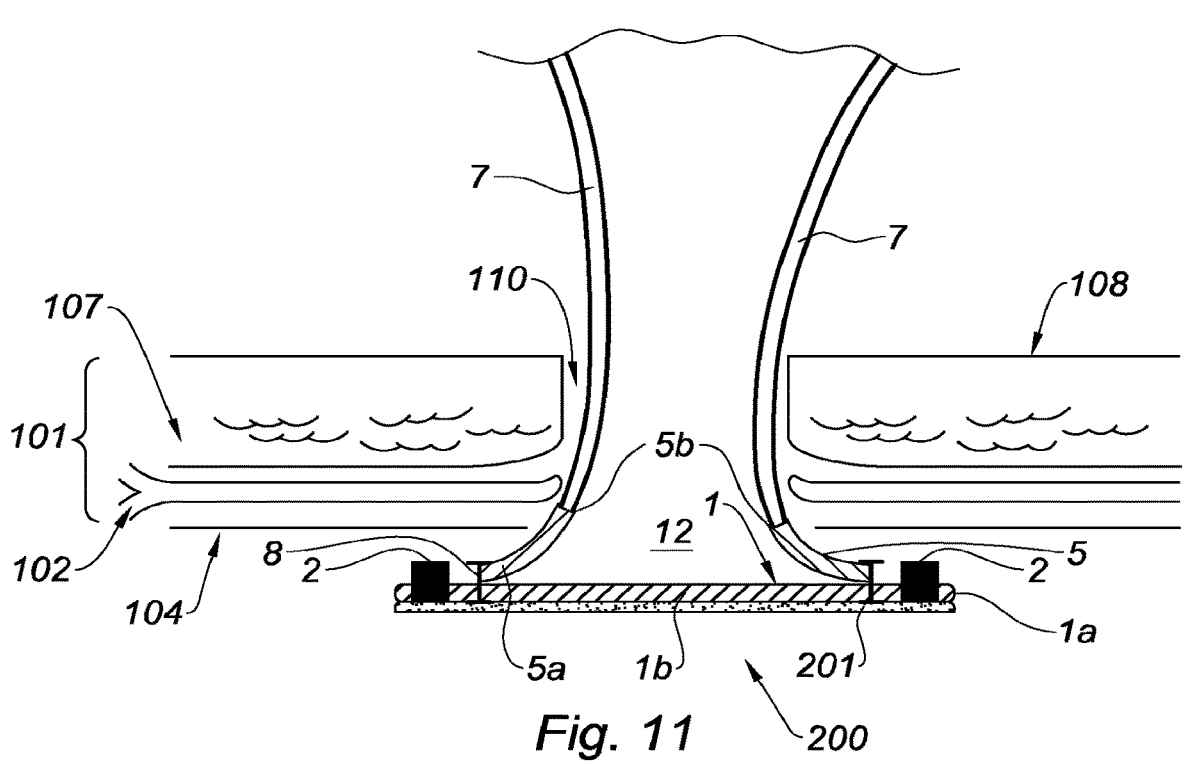
Figure 12:
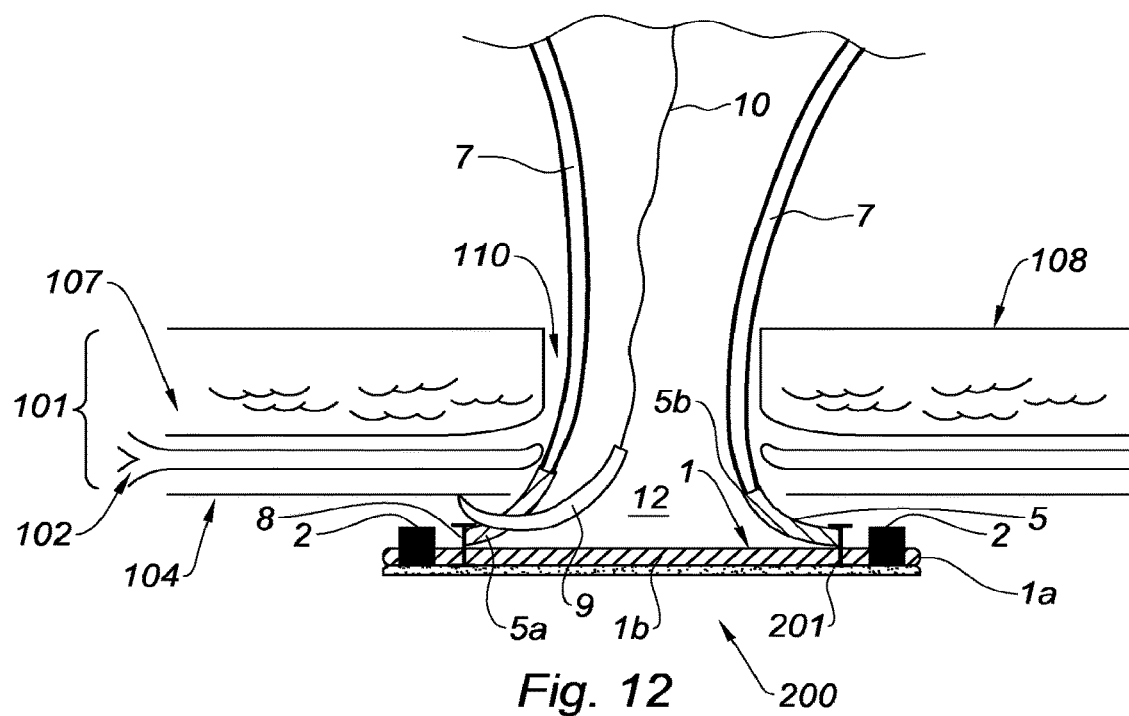
Figure 13:
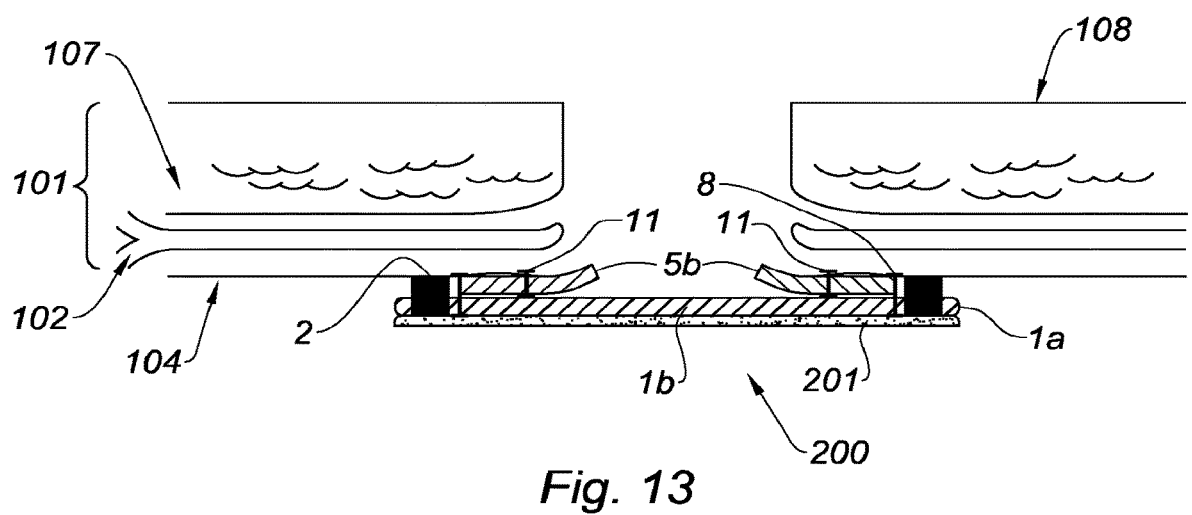

The present invention will emerge more clearly from the description given hereinafter and from the appended drawings, in which:

FIG. 1 is a representation in section of a median abdominal hernia or ventral rupture, FIG. 2 is a simplified view of the hernia from FIG. 1 after the surgeon has made an abdominal incision and removed the hernia sac, FIG. 3 is a top view of one embodiment of a mesh for a prosthesis of the invention, FIG. 4 is a top view of a reinforcing member for the prosthesis of the invention, FIGS. 5A to 5D are views of anchor pieces of the prosthesis of the invention, FIG. 6 is a top view of a first embodiment of the prosthesis of the invention, FIG. 7 is a top view of another embodiment of the prosthesis of the invention, FIG. 8 is a top view of another embodiment of the prosthesis of the invention, FIG. 9 is a top view of another embodiment of the prosthesis of the invention, FIG. 10 is a simplified sectional view of the introduction of the prosthesis from FIG. 8 into the hernia defect, FIG. 11 is a simplified sectional view of the positioning of the prosthesis from FIG. 8 after deployment thereof at the implantation site, FIG. 12 is a simplified sectional view of the fixing of the prosthesis from FIG. 8 to the abdominal wall, FIG. 13 is a view in section of the prosthesis from FIG. 8 when fixed to the biological tissues just before closure of the abdominal incision by the surgeon, FIG. 14-17 are top views showing the successive steps of the manufacturing process of a prosthesis of the invention comprising four anchor pieces of textile of identical mechanical properties.

FIG. 1 represents a hernia defect 100 of the abdominal wall 101 that is characterized by a break in the continuity of the aponeurosis 102 surrounding the straight muscles 103 and a passage through the peritoneum 104 forming a sac, the hernia sac 105, that contains either fat (epiploon) or part of the viscera 106, and which then presses on the fatty tissues 107 and is flush with the skin 108. One treatment of a hernia defect 100 entails replacing and retaining the viscera 106 in the abdominal cavity 109.

FIG. 2 shows the hernia defect 100 from FIG. 1 after the surgeon has made an incision in the skin 108, the abdominal wall 101 and the peritoneum 104 and has reduced the hernia sac. The viscera are not shown in FIG. 2: they have been pushed back into the abdominal cavity 109. The surgeon must now introduce into the abdominal cavity 109, via the incision 110 that has been made, a prosthesis for reinforcing the abdominal wall, before closing the incision 110 by means of sutures, for example. In the case of an umbilical hernia, the size of the incision 110 is particularly small, for example of the order of 1 to 4 cm diameter.

FIG. 3 represents a mesh 1 in the form of a disc usable with the reinforcing member from FIG. 4 and anchor pieces such as that from FIGS. 5A to 5D to produce a prosthesis of the invention.

The mesh 1 is made from a knitted, woven or non-woven arrangement of biocompatible threads. It may be bioresorbable, partly bioresorbable or permanent. The mesh is generally openwork, incorporating pores for better tissue integration. This mesh 1 is sufficiently flexible to be folded when the prosthesis is introduced into the abdominal cavity 109 via the incision 110. However, the mesh is generally a textile having no elasticity enabling it to return to a spread out configuration of its own accord after it has been folded up. The mesh 1 may be produced from a textile layer or a plurality of textile layers. The textile may be a two-dimensional or three-dimensional knitted fabric. Such meshes are well known to the person skilled in the art and are not described in more detail here. The mesh may be supplied in the form of a strip that is cut to the dimensions of the defect to be treated. In the example represented, the mesh 1 has the shape of a disc adapted to the shape of the incision 110 at the hernia defect 100 and delimited by an exterior peripheral edge 1a. In other embodiments, the mesh may be of oval shape. Alternatively, the mesh may be of rectangular or square shape.

FIG. 4 represents a reinforcing member of a prosthesis of the invention, suitable for the shape of the mesh 1 from FIG. 3: as is apparent from FIG. 4 and FIG. 6, the reinforcing member takes the form of a frame 2 substantially adopting the shape of the exterior peripheral edge 1a of the mesh 1. Thus the overall shape of the frame 2 is a circular ring. The frame 2 is provided with two hinge points 3a and 3b that are diametrically opposite in the example shown. The two hinge points (3a, 3b) make it possible to fold the frame 2, for example when force is applied by the surgeon, resulting in two globally identical parts. The hinge points (3a, 3b) preferably do not have any elasticity of their own: thus, once folded in two, the frame 2 can be unfolded only by the action of an external force, for example exerted by the surgeon.

The frame 2 thus consists of two parts, namely two semicircles 2a and 2b, connected together by two hinge points (3a, 3b). As seen in FIG. 4, the respective ends (2c; 2d) of the semicircles 2a and 2b are blunted or rounded to prevent trauma when implanting the prosthesis. In the example shown, the two semicircles 2a and 2b are symmetrical: the two hinge points (3a; 3b) define a median line M passing through the centre of the circle delimited by the frame and also through the centre of the mesh 1 when the frame 2 is fixed to the mesh 1, as shown in FIG. 6. Thus the mesh 1 may be folded in two even when fitted with the frame 2: consequently, as will become apparent in the remainder of the description, the prosthesis may be folded. Similarly, given the configuration of the frame 2 in two parts and the absence of any elasticity of the frame 2 and its hinge points (3a, 3b), the prosthesis is able to adopt only two configurations: either a flat and spread out configuration or a folded in two configuration. As explained later, the fact that the prosthesis can adopt only two configurations facilitates the task of the surgeon, who can immediately determine if the prosthesis is in its spread out configuration or not.

As seen in FIGS. 4 and 6, the frame 2 is an undulating ring set back from the exterior peripheral edge 1a, consisting of undulations 4. Referring to FIG. 6 in particular, the exterior peripheral edge 1a of the mesh extends some distance beyond the exterior contour of the frame 2: this distance may be greater than or equal to 1 mm, for example. As will become apparent from the description given hereinafter, the location of the frame 2, slightly set back from the exterior peripheral edge 1a, facilitates efficacious fixing of the prosthesis to the abdominal wall, in particular in an area located more or less half way between the centre and the edge of the mesh, this area being adjacent to the interior contour of the frame 2.

The undulations 4 of the frame 2 may be regular or not. In particular, in the example shown, the frame 2 is in the form of a flat ribbon of material forming undulations 4 in the plane of the frame 2, which is substantially the plane of the prosthesis. As will become apparent in the remainder of the description, such a shape imparts to the frame 2 great flexibility in the plane of the frame 2 and thus in the plane of the prosthesis: it is thus possible to suture part of the prosthesis at a given place, without rocking or deforming the prosthesis as a whole: the deformation created at the location of the suture is smoothed out by the undulations 4 of the frame 2 over the whole of the periphery of the prosthesis. In addition, the frame 2 shows a rigidity along its section, so that it neither deforms radially in the outward nor in the inward directions.

Materials suitable for producing the reinforcing member of the prosthesis of the invention may be any biocompatible materials having some rigidity so as to respond to the expectations disclosed above.

The frame 2 can thus be produced in any biocompatible material, bioresorbable or not. In a preferred embodiment, it is made in bioresorbable material. In the present application, the term "bioresorbable" refers to the characteristic whereby a material is absorbed by biological tissues and disappears in vivo after a given period, which may vary from one day to several months, for example, depending on the chemical nature of the material.

Bioresorbable materials suitable for the fabrication of the reinforcing member of the prosthesis of the present invention include polylactic acid (PLA), polycaprolactone (PCL), polydioxanone (PDO), trimethylene carbonate (TMC), polyvinyl alcohol (PVA), polyhydroxyalkanoate (PHA), oxidized cellulose, polyglycolic acid (PGA), copolymers of these materials and mixtures thereof. Bioresorbable materials suitable for the fabrication of the reinforcing member of the prosthesis of the invention include polyester (glycolid, dioxanone, trimethylene carbonate) available from the company Covidien under the trade name "BIOSYN®" and polyester (glycolid, caprolactone, trimethylene carbonate, lactid) available commercially from the company Covidien under the trade name "CAPROSYN®".

Non-bioresorbable materials suitable for the fabrication of the reinforcing member of the prosthesis of the present invention include polypropylene, polyesters such as polyethylene terephthalate, polyamide, silicone, polyetheretherketone (PEEK), polyaryletheretherketone (PAEK) and mixtures thereof.

Each part of the reinforcing member of the prosthesis of the invention may be made in one piece, for example, by injection moulding one or more biocompatible thermoplastic or thermosetting materials. The hinge points (3a, 3b) of the frame 2 may be produced in the same material as the rest of the frame: these hinge points (3a, 3b) take the form for example of very thin bridges of material in order to enable folding of the frame 2 without causing separation of the two parts joined together by these bridges.

With reference to FIGS. 5A to 5D are shown, on their own, examples of anchor pieces 5 suitable for the prosthesis of the invention, each provided with a thread-shaped element (6, 7). The anchor pieces may show any geometrical shape, for example triangular, squared, semicircular. They may be identical or different for a single prosthesis.

In embodiments, such as those shown on FIGS. 5A to 5 B, the anchor pieces 5 show a geometrical shape where at least one side has a length greater than or equal to that of the other sides. Thus, with reference to FIG. 5A, the anchor piece 5 has the shape of a triangle. In this example, the triangle is isosceles and the basis B of the triangle is the side having the greatest length. As will appear hereinafter, the longest side of the anchor piece 5 will form the fixed part 5a of the anchor piece 5 while the area located around the summit C opposed to that basis B will form the free part 5b of the anchor piece 5. In the same way, with reference to FIG. 5B, the anchor piece 5 having globally the shape of a semi-disc, the diameter D forms the side of greater length of the anchor piece and will therefore form the fixed part 5a of the anchor piece, while the rounded part forms the free part 5b of the anchor piece 5. With reference to FIG. 5C, the anchor piece has globally the shape of an isosceles triangle the basis of which is an arc of circle: this basis will form the fixed part 5a of the anchor piece, while the area located around the summit opposed to that arc of circle will form the free part 5b of the anchor piece 5.

On FIG. 5D is shown an anchor piece 5 of trapezoid shape, the parallel sides of which show an arc of circle shape: the longest arc of circle forms the fixed part 5a of the anchor piece, while the area located around the shortest arc of circle forms the free part 5b of the anchor piece.

On FIGS. 5A to 5B, the free part 5b of each anchor piece is linked to a thread-shaped element. In the context of the present application, by "thread-shaped element", is meant a flexible and elongated element, the length of which is much more greater than its thickness and its width, the contour of the cross section of which is globally circular: examples of thread-shaped elements of the invention may be a thread on its own, composite or not, or several threads, for example arranged together to make a braid, a tube, and combinations thereof. In embodiments, the thread-shaped elements are selected from threads, tubes and combinations thereof.

As will be apparent from the following detailed description, the thread-shaped element is intended to allow the surgeon to pull on the anchor piece linked thereto in order to expand, orientate and position the prosthesis when said prosthesis is put in place: preferably, the surgeon will pull simultaneously on the thread-shaped elements of the at least two anchor pieces which are present in order to centre and counterbalance the prosthesis with respect to the defect to be treated.

With reference to FIG. 5A, the free part 5*b* of the anchor piece is linked to a thread 6 passing through said free part 5*b*. On the example shown, the thread 6 forms a loop. Alternatively, the thread 6 may be attached by one of its ends to the free part 5*b* of the anchor piece 5. With reference to FIG. 5B, the free part 5*b* of the anchor piece is also linked to a thread 6 passing through said free part 5*b*, said thread 6 forming a loop at the location of said free part 5*b*, the two strands of the loop being further brought together within a tube 7.

With reference to FIG. 5C, the free part 5*b* of the anchor piece 5 is linked to a tube 7: on the example shown, the two ends 7*a* and 7*b* of tube 7 are attached to the free part 5*b* and the tube 7 forms a loop. With reference to FIG. 5D, the free part 5*b* of the anchor piece 5 is linked to one end 7*a* of a tube 7.

The tube 7 is flexible and, because of its hollow structure, necessitating a certain outer diameter, for example equal to or greater than 3 mm, it shows a quite important outer surface capable of being in contact with the margins of the defect, this allowing decreasing dramatically the potential traumatic effect due to the contact of the tube 7 with the margins of the defect. The flexible tube 7 may be in plastic material, silicone, or in a combination of these materials.

The anchor pieces 5 of the prosthesis of the invention are made of a suturable material: in the context of the present application, it is hereby meant that the anchor piece 5 is capable of being linked to, or passed through by, a thread-shaped element, such as a thread 6 or a tube 7, without being torn off when a user, such as a surgeon for example, exerts a moderate tension on said thread-shaped element, such as the necessary tension for orientating and/or positioning the prosthesis in the implantation site, as described hereinafter. The anchor pieces 5 may be made of any biocompatible suturable material giving them the necessary flexibility for being grasped by the surgeon when the prosthesis is put in place, as will be described hereinafter.

The anchor piece 5 may be under the form of a textile, either knitted, woven or nonwoven, open worked or not; alternatively or in addition, the anchor piece may be under the form of a film or a sheet of material, as long as this textile, film and/or sheet of material is not torn off under the effect of the moderate tension as described above exerted on a thread-shaped element linked to, or passing through, said textile, film and/or sheet.

As will be apparent from the following description, the anchor pieces are useful to the surgeon for facilitating the positioning of the prosthesis in the centre of the defect to be treated, and for attaching the prosthesis to the biological tissues. The anchor pieces also form the parts of the prosthesis by which said prosthesis is sutured to the abdominal wall.

With reference to FIG. 6 is shown a prosthesis 200 according to the invention, comprising the mesh 1 of FIG. 3, the reinforcing member 2 of FIG. 4 and two anchor pieces 5 similar to the anchor piece of FIG. 5C, each anchor piece 5 being on that FIG. 6 linked to a thread-shaped element under the form of a thread 6.

As is apparent from this FIG. 6, the anchor pieces 5 are each attached to the mesh 1 by their longer side forming the fixed part 5*a* of the anchor piece: the fixing of each anchor piece 5 by its longer side allows a more reliable fixation. Moreover, the fixed part 5*a* of each anchor piece 5 is attached along the direction of the line P which is perpendicular to the segment S linking the centre of the mesh and the point of fixation of each piece in the plane of the mesh. The fixed part 5*a* or longer side of each anchor piece is fixed to the mesh for example by sewing. Alternatively, it may be fixed to the mesh 1 by gluing, welding or by means of the reinforcing member 2.

The anchor pieces 5 being fixed to the mesh by their longest side, they do not impede the surgeon at the time of the prosthesis is implanted. On FIG. 6, the two anchor pieces 5 are fixed to two diametrically opposed places of an inner perimeter of the ring 2, said two places being spaced by 90° from each of said two hinge points (3*a*, 3*b*).

With reference to FIGS. 7 to 9 are shown prosthesis 200 of the invention made with the mesh 1 from FIG. 3, the frame 2 from FIG. 4 and four anchor pieces 5 from FIG. 5A, linked to various thread-shaped elements.

In these embodiments, the four anchor pieces 5 are arranged regularly along an inner perimeter of the ring formed by the frame 2 so that two anchor pieces 5 are located on one side of the folding line M and the two other anchor pieces are located on the other side of the folding line M: the four anchor pieces therefore counterbalance one another. Each anchor piece 5 is fixed to the mesh 1 by its fixed part 5*a*, the free parts 5*b* being left flying and forming flaps. For example, each fixed part 5*a* is attached to the mesh 1 by a seaming 8. Moreover, a single thread-shaped element (6, 7) links together the free parts 5*b* of two anchor pieces 5 located on the same side of the folding line M.

With reference to FIG. 7, the thread-shaped element is under the form of a combination of a thread 6 and a tube 7: the thread 6 forms a loop at the place of the free part 5*b* of the anchor piece it is linked to, the two strands of the loop being brought together within a tube 7 at the place of grasping of the thread-shaped element by the surgeon. Such an embodiment allows an easier and more comfortable grasping of the thread-shaped element by the surgeon.

With reference to FIG. 8, the thread-shaped element is under the form of a tube 7: the first end 7*a* of the tube 7 is attached to the free part of a first anchor piece 5 while the second end 7*b* of the same tube 7 is attached to the free part 5*b* of the adjacent anchor piece located on the same side of the folding line M as the first anchor piece 5. Such an embodiment, in which the thread-shaped element is a tube 7, allows an easier and more comfortable grasping of the thread-shaped element, while limiting the risk of trauma when the thread-shaped element contacts the margins of the defect to be treated at the time of positioning the prosthesis 200. The tube 7 may itself contain one or several threads.

With reference to FIG. 9, the thread-shaped element is under the form of a thread 6 forming a loop at the place of the free part 5*b* of a first anchor piece 5 and at the place of the free part 5*b* of a adjacent anchor piece located on the same side of the folding line M as the first anchor piece 5.

The presence of the four anchor pieces 5, regularly distributed as described above in FIGS. 7 to 10, and of the thread-shaped elements linking anchor pieces 5 by pairs enables the surgeon to optimally spread out the prosthesis 200 on the implantation site and to balance the tension between the various anchor pieces 5 at the time of positioning the prosthesis 200 and to centre the latter prosthesis better relative to the defect to be closed.

In one embodiment of the prosthesis 200 not shown, the reinforcing member, namely the frame 2, is welded directly to the mesh 1 and to the fixed parts 5a of anchor pieces 5. Thus the frame 2 is fastened both to the mesh 1 and to the anchor pieces 5.

In the FIG. 8 embodiment, the face of the mesh 1 opposite that including the anchor pieces 5 is covered by a non-adherent coating 201. Such a non-adherent coating makes it possible to avoid in particular the formation of unwanted severe post-operative fibrous adhesions; once the prosthesis 200 has been implanted, the face of the prosthesis 200 covered by the non-adherent coating 201 faces the abdominal cavity 109.

The non-adherent coating or material is chosen from bioresorbable materials, non-bioresorbable materials and mixtures thereof. The non-bioresorbable non-adherent materials may be chosen from polytetrafluoroethylene, polyethylene glycol, polysiloxane, polyurethane, and mixtures thereof.

Said non-adherent coating or material is preferably bioresorbable: bioresorbable materials suitable for said non-adherent coating may be chosen from collagen, oxidized cellulose, polyacrylate, trimethylene carbonate, caprolactone, dioxanone, glycolic acid, lactic acid, glycolide, lactide, polysaccharide, for example chitosan, polyglucuronic acid, hyaluronic acid, dextran and mixtures thereof.

The non-adherent coating makes it possible to protect the mesh 1 of the prosthesis 200 at least during the initial scar formation phase, i.e. the mesh 1 is not exposed to inflammatory cells, such as granulocytes, monocytes, macrophages or the giant multinucleated cells generally activated by surgery. At least during the initial scar formation phase, the duration of which may vary from about 5 days to about 10 days, only the non-adherent coating is accessible to the various factors such as proteins, enzymes, cytokines or inflammatory cells.

If the non-adherent coating consists of non-resorbable materials, it thus protects the mesh 1 before and after implantation and throughout the duration of implantation of the prosthesis 200.

Moreover, thanks to the non-adherent coating, surrounding fragile tissues, such as the hollow viscera, for example, are protected, in particular from unwanted severe post-operative fibrous adhesion.

If the non-adherent material includes a bioresorbable material, it is preferable to choose a bioresorbable material that is not resorbed in less than a few days in order for the non-adherent coating to be able to fulfil its function of protecting the intestine and hollow organs during the days following surgery until cellular rehabilitation of the prosthesis takes over protecting these fragile organs.

Because of its two-part reinforcing member, namely the frame 2 consisting of the two semicircles 2a and 2b in the example shown, connected together by hinge points 3a, 3b, the prosthesis 200 of the invention may adopt a folded configuration after the surgeon folds it along the folding line M. Thus to implant the prosthesis 200 the surgeon folds it in two so that it occupies a smaller volume, which facilitates introduction of the prosthesis into the hernia defect 100 (see FIG. 2) by the surgeon.

The mesh 1 and the non-adherent coating 201 are sufficiently flexible to follow successive deformations of the prosthesis 200 as the latter is introduced to the implantation site.

FIGS. 14-17 describe various steps of a method for manufacturing an embodiment of a prosthesis 210 of the invention made with the mesh 1 of FIG. 3, the frame 2 of FIG. 4 and four anchor pieces 215. For clarity's sake, the thread-shaped elements are not shown on FIGS. 14-17: these thread-shaped elements may be any one of FIGS. 6-9 and may be attached to said anchor pieces 215 as described above.

As will appear from the description below, the four anchor pieces 215 of prosthesis 210 are arranged symmetrically along the interior contour of the ring formed by the frame 2, and they all have the same mechanical properties.

The manufacturing process of such embodiments will now be described with reference to FIGS. 14-17.

Figure 14:
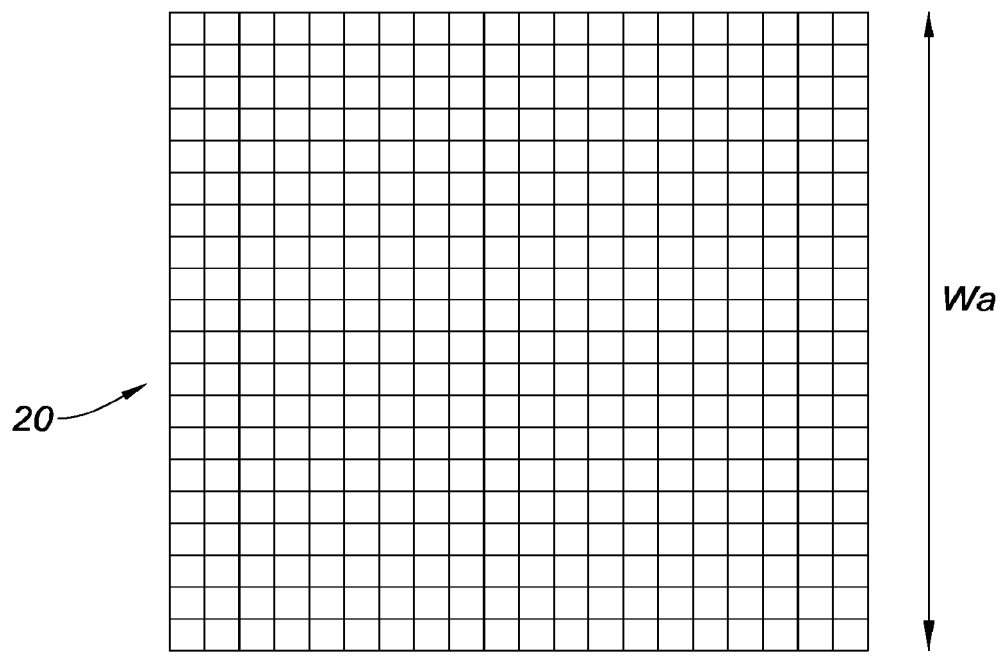
Figure 17:
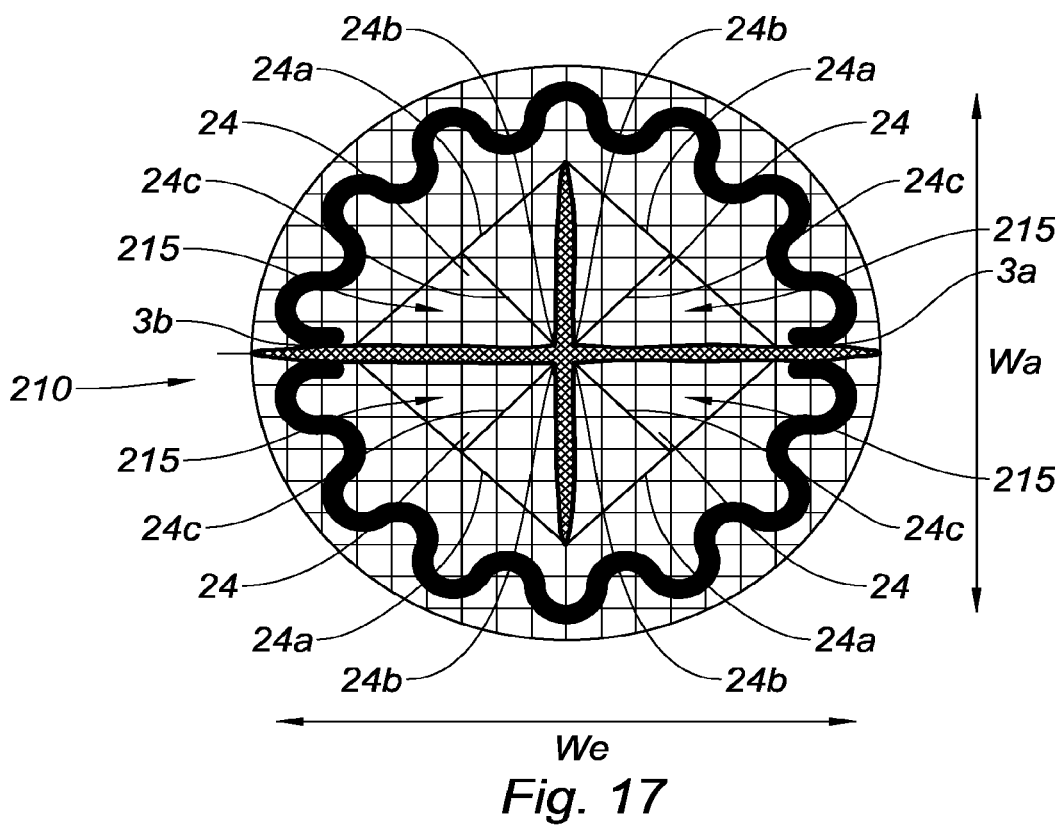

With reference to FIG. 14, is shown a textile 20 for forming the anchor pieces 215 of the prosthesis 210 (see FIG. 17). On the example shown, the textile 20 has the shape of a square, the length of one side of the square being greater than the greater diameter of the intended resulting prosthesis 210. This textile 20 may be identical to that forming the mesh 1 or different. The textile 20 is for example produced on a knitting machine and has a warp direction Wa and a weft direction We, as shown on this FIG. 14. The textile 20 may have different mechanical properties, such as elongation and tensile strength, along its warp direction Wa and along its weft direction We.

Preferably, the textile 20 has a colour different from that of the mesh 1.

Figure 15:
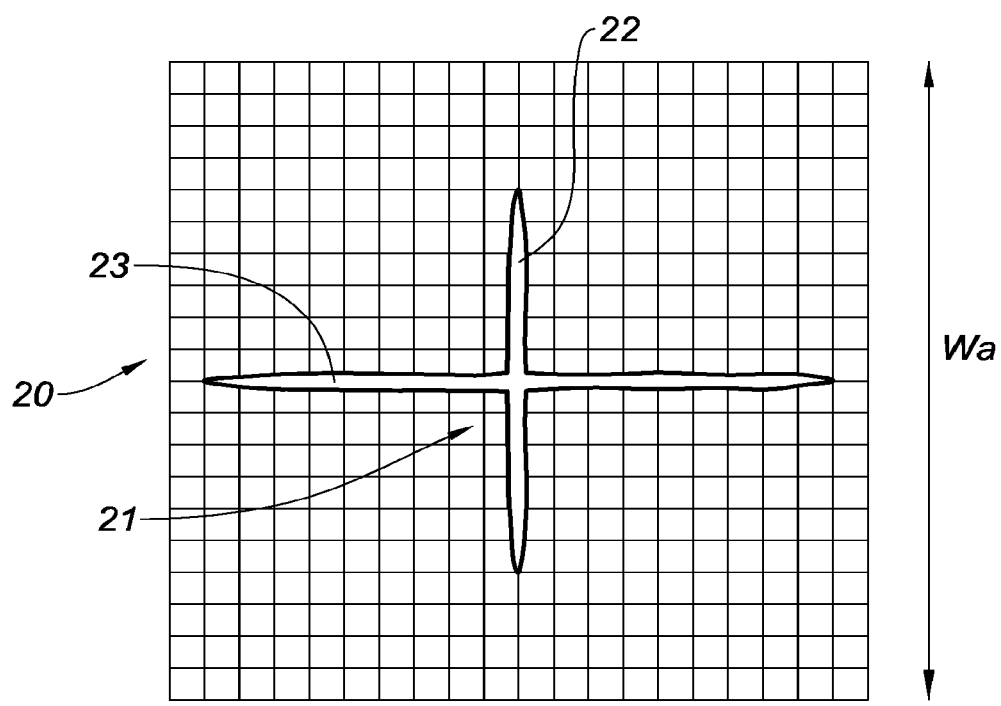

In order to proceed with the manufacturing of the four anchor pieces 215, a cutting 21 having the shape of a cross with two perpendicular branches (22, 23) is completed on textile 20, with one branch 22 of the cross parallel to the warp direction Wa and the other branch 23 of the cross parallel to the weft direction We, as shown on FIG. 15. The branches of the cross may be of identical lengths or not. On the example shown on FIG. 15, the length of the branch 22 parallel to the warp direction Wa is smaller than the length of the branch 23 parallel to the weft direction. In addition, on this example and as will appear from FIG. 16, the length of the branch 22 parallel to the warp direction Wa is smaller than the diameter of the internal perimeter of the frame 2, whereas the length of the branch 23 parallel to the weft direction is greater than the diameter of the outer perimeter of the frame 2.

In a further step, the textile 20 is laid upon a piece of mesh 1, for example of similar square shape and dimensions as the textile 20, and the frame 2 of FIG. 4 is then welded to both the mesh 1 and the textile 20.

Figure 16:
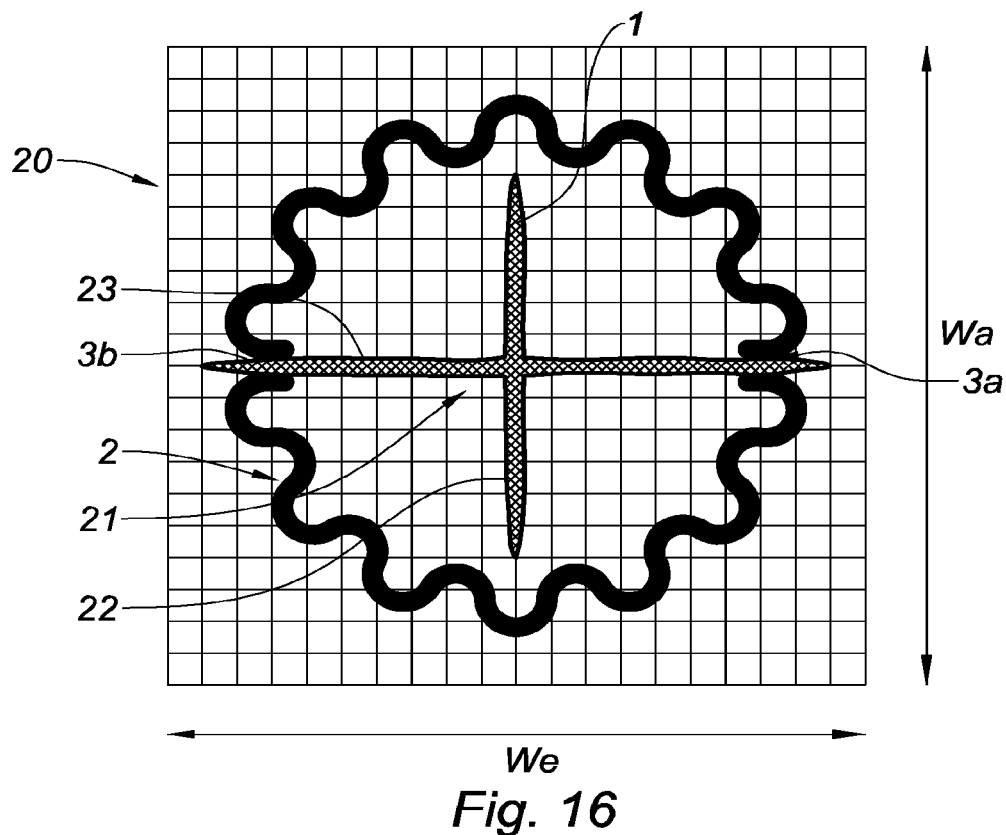

As shown on FIG. 16, the frame 2 is welded on mesh 1 and textile 20 so that the greater branch 23 of the cutting 21 is applied on the folding line M defined by the frame 2 (see FIG. 4) and extends beyond the hinge points (3a, 3b) of the frame 2, whereas the smaller branch 22 of the cutting 21 does not reach the frame 2. Such an embodiment allows a better efficiency of the frame 2, which may not be damaged by residual filaments coming from the cutting of branch 22 when said frame 2 is welded on both the mesh 1 and the textile 20.

Once the frame 2 is welded, the disc-shape prosthesis 210 may be manufactured by cutting the mesh 1 and textile 20 in excess beyond the outer peripheral border of the frame 2, as shown on FIG. 17. As appears from this Figure, the frame 2 forms together with the cross-shaped cutting 21 four isosceles triangles 24, more or less fixed to the frame 2 by their respective base 24a and free at their vertex angle 24b. These four isosceles triangles 24 of textile 20 form the anchor pieces 215 of the prosthesis 210.

As mentioned above, a thread-shaped element (not shown) may then be attached to the free vertex angle 24b of each triangle 24 by any fixation means such as those described above at FIGS. 6-9, in line with the direction defined by the altitude 24c drawn from the vertex angle 24b of each triangle 24.

Because of the specific cross-shaped cutting 21, with one branch parallel to the warp direction Wa and the other branch parallel to the weft direction We, all four isosceles triangles 24 of textile 20 are identical and they all show the same mechanical properties, such as elongation properties and tensile strength properties, each in the direction of its altitude 24c corresponding to the centripetal direction of the disc-shape prosthesis 210, regardless from the fact that the initial elongation and tensile strength properties of the textile 20 in its warp direction Wa were identical or not to its initial elongation and tensile strength properties in the weft direction We.

Indeed, because of the location of the cutting 21 with respect to the frame 2 during the welding step, the altitude direction or centripetal direction for each triangle 24 forms an angle of 45° with respect to both warp and weft directions of the initial textile 20.

As a consequence, all four anchor pieces 215 show the same mechanical properties, in particular elongation properties and tensile strength properties, in the direction corresponding to the direction of the altitude 24c of each triangle 24, in other words in the direction corresponding to the direction of the traction exerted by the surgeon when he pulls on the thread-shaped element (not shown) in order to put the prosthesis in place and to fix it to the abdominal wall.

As a consequence, when the surgeon pulls on the thread-shaped element at the time he puts the prosthesis 210 in place and fixes it to the abdominal wall, all anchor pieces 215 react similarly and the traction exerted by the surgeon on the whole prosthesis 210 via the four anchor pieces is equally distributed. The prosthesis 210 is therefore properly positioned. In addition, because the four isosceles triangles 24 of textile 20 have a colour different from that of the mesh 1, the surgeon readily identifies the stitching line as defined above. The step of fixing the prosthesis 210 to the abdominal wall is therefore facilitated.

The method of manufacturing the prosthesis 210 described above is very simple and allows starting from a single piece of textile 20 for manufacturing the four anchor pieces 215.

Alternatively, the prosthesis 210 may be manufactured by preparing initially four separate triangles 24 of textile 20 and welding each triangle 24 to the mesh 1 via the frame 2, or alternatively by preparing two pieces of semi-discs of textile 20, completing a perpendicular cutting on each semi-disc and welding the two cut semi-discs to the mesh via the frame 2.

Like the prosthesis 200 of FIGS. 1-13, the prosthesis 210 of FIG. 17 may be coated on the face of the mesh 1 opposite that including the anchor pieces 215 with a non-adherent coating 201.

The fitting of a prosthesis of the invention, for example the prosthesis 200 from FIG. 8, is described next with reference to FIGS. 10 to 13. Although not described, the fitting of the prosthesis 210 of FIG. 17 may be completed in the same manner as that described hereinafter for prosthesis 200 of FIG. 8.

After making the incision 110 described with reference to FIG. 2, the surgeon grasps the prosthesis 200 from FIG. 8, covered with a non-adherent coating 201 on the face of the mesh 1 opposite that including the anchor pieces 5, and applies force to the prosthesis 200 with his fingers to fold it along the folding line M. Because of the presence of the two hinge points 3a and 3b, this operation is without difficulty and totally independent of the elastic or non-elastic nature of the frame 2. In the embodiment shown, the prosthesis 200 being a disc, it is folded along one of its diameters, resulting in two identical parts. In this folded configuration, the prosthesis 200 occupies a small volume and the surgeon may easily introduce it into the abdominal cavity 109, as shown in FIG. 10, while holding the thread-shaped elements, in other words the tubes 7 in the example shown, outside the body of the patient. Because of their structure, the thread-shaped elements allow limiting the volume of the various elements which need to be passed through the hernia defect. For clarity, the fingers of the surgeon are not represented in FIGS. 10 to 13.

Once the prosthesis 200 is in the abdominal cavity 109, the surgeon releases the pressure on it. It is the surgeon who manually deploys the prosthesis 200 in a perfectly tensioned and spread out configuration. Thus, the prosthesis 200 being able to adopt only two positions, namely folded in two or spread out, the surgeon is certain that the prosthesis is perfectly spread out from the moment of unfolding the prosthesis 200.

In the next step, as shown in FIG. 11, the surgeon uses the thread-shaped elements, i.e. the tubes 7, both to centre the prosthesis 200 relative to the incision 110 and to press the prosthesis 200 against the abdominal wall (101, 104). To this end, the surgeon pulls the tubes 7 toward the exterior of the body of the patient and in opposite directions. The surface of the tubes 7 capable of being in contact with the margins of the defect being quite important, the risk of trauma is low. Moreover, the distribution of the anchor pieces 5 as explained above allows balancing and centring the prosthesis 200 on the defect to be treated while pressing said prosthesis on the abdominal wall. Thus the prosthesis 200 is spread perfectly and there is no risk of the viscera being disposed between the anchor pieces 5 and the abdominal wall (101, 104).

Once the prosthesis 200 is correctly positioned relative to the hernia defect, the surgeon raises a part of the edge of the hernia with the help of the tubes 7 and thus uncovers a central area 12 in the vicinity of the prosthesis 200, delimited overall by the anchor pieces 5, which area the surgeon may easily view and in which the surgeon is able to work easily.

In an embodiment, the tubes 7 are flexible and semi-rigid. Such a semi-rigidity of the tubes 7 allows maintaining the anchor pieces 5 to which they are linked under slight tension, without having to apply any particular tension on these tubes: as such, once the surgeon has raised the edges of the hernia defect by pulling on the flexible and semi-rigid tubes 7 in order to uncover a working area, he can release the tension on the tubes 7: the anchor pieces 5 remain under slight tension and maintain the edges of the defect in a raised position.

In embodiments, the anchor pieces 5 are of a colour different than that of the mesh 1: indeed, because the fixation area of the prosthesis 200 to the abdominal wall (101, 104) is located more or less in the middle between the centre 1b of the mesh 1 and the edge of the mesh, the surgeon can differentiate the different colours between the various elements forming the prosthesis 200 and thus easily identify the anchor pieces 5 he has to suture: such a thing is not possible with the prosthesis of the prior art intended to be fixed to the abdominal wall at their periphery. In particular, the colour difference between the anchor pieces 5 and the mesh 1 defines a line, said line pointing out to the surgeon where to complete the stitches for fixing the prosthesis 200 to the abdominal wall. This fixing line, or stitching line, globally corresponds to the interior contour of the frame 2. Also, for the same reasons, the thread-shaped elements, like the tubes 7, may be of a colour different from that of the mesh and from that of the anchor pieces 5.

In a following step, as shown in FIG. 12, the surgeon proceeds to fix the prosthesis 200 to the biological tissues by using a needle 9 and a suture 10 to suture the free part 5b of each anchor piece 5 to the abdominal wall 101, 104 within the central working area 12. During this step, the whole of the prosthesis 200 remains perfectly spread out and perfectly pressed onto the abdominal wall 104, notably by virtue of the presence of the undulations 4 of the frame 2, which smooth out deformations caused by the surgeon in the area of the prosthesis 200 that is in the process of being sutured. The surgeon may execute one or more stitches 11 (see FIG. 13) for each free part 5b of the four anchor pieces 5.

As may be seen in FIG. 13, the structure of the prosthesis 200 of the invention enables the surgeon to place the stitches 11 in an area situated more or less in the middle between the centre of the mesh 1 and the exterior peripheral edge 1a thereof; thus the surgeon does not have to execute stitches at the exterior peripheral edge 1a of the mesh 1, which can be viewed only with difficulty because of the small size of the incision 110. The mesh 1 nevertheless remains perfectly pressed against the abdominal wall 104 along this peripheral edge 1a because of the presence of the frame 2. Nevertheless, because of the structure of the prosthesis 200 of the invention, the stitches 11 are advantageously situated at some distance from the defect, in particular in an area more or less in the middle between the centre 1b of the mesh (which is the location of the hernia defect) and the edge 1a of the mesh, at a location where the biological tissues are often healthier and less fragile than at the margin of the defect. The stitches 11 may for example be U-shaped, i.e. obtained with a thread provided with a needle at each of its ends.

Once the surgeon has executed the necessary stitches 11 over all the anchor pieces 5, he cuts each thread-shaped element, here each tube 7, at its junction with the free part 5b of the anchor piece 5 in order to retain at the implantation site only the anchor pieces 5, as shown in FIG. 13. This figure shows the stitches 11 that fix the free parts 5b of the anchor pieces 5 to the abdominal wall 104. As may be seen in FIG. 13, the prosthesis 200 is thus perfectly deployed, spread out and pressed against the abdominal wall (101, 104) with no risk of trapping viscera between the prosthesis 200 and the abdominal wall (101, 104).

The surgeon then has only to close the incision 110 in the conventional way for small size hernias, i.e. by stitches.

The prosthesis of the invention is particularly simple to install, the surgeon being easily able to uncover a comfortable and non obstructed working area, despite the restricted size of the implantation site. The fitting of the prosthesis of the invention is also particularly reliable, all risk of trapping the viscera being avoided. A prosthesis of the invention is particularly suitable for treating umbilical hernias where the abdominal incision made is of small size. The prosthesis of the invention is adapted to adopt a configuration in which it occupies a particularly small volume facilitating its introduction into the abdominal cavity via a small incision without necessitating the use of any dedicated ancillary device. Thanks to its particular structure, the prosthesis of the invention may be spread out and pressed onto the abdominal wall efficaciously, also without necessitating the use of a dedicated tool to assist spreading it and it may be attached securely to the abdominal wall at an area located more or less in the middle between the centre of the prosthesis and its periphery: the surgeon is therefore prevented from having to make stitches at far distance places, such as the periphery of the prosthesis, that he cannot see. The prosthesis of the invention thus makes it possible to treat a hernia, in particular an umbilical hernia, efficaciously, simply and rapidly, minimizing the risk of relapse.

The invention claimed is:

1. A prosthesis comprising:
   at least one flexible mesh defined by a peripheral exterior edge,
   at least one reinforcing frame secured to the mesh and substantially adopting a shape of the peripheral exterior edge of the mesh, the frame being set back from the peripheral exterior edge and defining an inner perimeter, the frame being provided with two hinge points, a folding line passing through the two hinge points also passing through a center of the mesh for folding the mesh in two
   at least two anchor pieces located on a first face of the mesh on either side of the folding line, each anchor piece including a fixed part linked to the mesh and a free part linked to at least one thread-shaped element, wherein at least one anchor piece has a shape selected from the group consisting of a semi-disc a base of which represents a diameter of the disc, an isosceles triangle a base of which is an arc of a circle, or a trapezoidal shape.

2. A prosthesis according to claim 1, wherein each anchor piece is linked to the mesh by its longest side, along a direction perpendicular to a segment linking the center of the mesh and a point of fixation of the piece in a plane of the mesh.

3. A prosthesis according to claim 1, wherein the at least one thread-shaped elements are selected from threads, flexible tubes and combinations thereof.

4. A prosthesis according to claim 3, wherein the thread-shaped elements are flexible tubes.

5. A prosthesis according to claim 4, wherein the flexible tubes are semi-rigid.

6. A prosthesis according to claim 1, wherein the frame set back from the peripheral external edge is of serpentine shape forming undulations.

7. A prosthesis according to claim 6, wherein the frame takes the form of a flat ribbon forming undulations substantially in a plane of the mesh.

8. A prosthesis according to claim 1, wherein the reinforcing frame is produced in bioresorbable material.

9. A prosthesis according to claim 1, wherein the mesh is disc-shaped, the reinforcing frame being substantially in a form of a circular ring.

10. A prosthesis according to claim 9, wherein the at least two anchor pieces are fixed to diametrically opposed places of an inner perimeter of the ring, the two places being spaced by 90° from each of the two hinge points.

11. A prosthesis according to claim 9, wherein the prosthesis comprises four anchor pieces distributed substantially regularly along an inner perimeter of the ring so that two anchor pieces are located on one side of the folding line and the other two anchor pieces are located on the other side of the folding line.

12. A prosthesis according to claim 11, wherein a single thread-shaped element links together the free parts of two anchor pieces located on the same side of the folding line.

13. A prosthesis according to claim 11, wherein all four anchor pieces are under the form of isosceles triangles of textile, all four triangles showing identical elongation and tensile strength properties in a centripetal direction.

14. A prosthesis according to claim 1, wherein the anchor pieces have a color different than that of the mesh.

15. A prosthesis according to claim 1, wherein the thread-shaped elements have a color different than that of the mesh and than that of the anchor pieces.

16. A prosthesis according to claim 1, wherein the face of the mesh opposite that including the anchor pieces is covered by a non-adherent coating.

17. A prosthesis according to claim 1, wherein the at least two anchor pieces are separate individual pieces.

18. A prosthesis according to claim 1, wherein the at least one thread-shaped element comprises at least one thread linked to the free part of the at least two anchor pieces, wherein the at least one thread passes through at least one flexible tube between the free part of the at least two anchor pieces.

19. A prosthesis according to claim 1, wherein the frame is rigid and the hinge points do not have any elasticity.

20. A prosthesis according to claim 19, wherein the prosthesis is configured to adopt only two configurations including a flat and spread out first configuration and a fold evenly in two configuration.

* * * * *